United States Patent [19]

Weigand et al.

[11] 4,023,572

[45] May 17, 1977

[54] MILLING TOOL FOR PREPARING A JOINT SOCKET IN THE PROSTHETIC REPLACEMENT OF A JOINT

[76] Inventors: Hanfried Weigand, Sudring 106, 65 Mainz-Bretzenheim; Bernhard Bellmann, Moselstr. 7, 6102 Pfungstadt; Henning Müller-Gerbes, Pfungstadter Str. 35, 61 Darmstadt-Eberstadt; Wolfhard Sack, Berliner Str. 1, 6081 Wolfskehlen; Paul-Heinz Theimert, Gerhart-Hauptmann-Str. 10, 6101 Weiterstadt, all of Germany

[22] Filed: Aug. 5, 1975

[21] Appl. No.: 602,061

[30] Foreign Application Priority Data

Aug. 6, 1974 Germany .......................... 2437772
Jan. 11, 1975 Germany .......................... 2500959

[52] U.S. Cl. .................................. 128/305; 29/78; 30/276; 30/279 R
[51] Int. Cl.² ......................................... A61B 17/32
[58] Field of Search ............ 29/78, 103 R; 30/276, 30/279 R; 76/101 S, 101 M; 128/305 R, 305

[56] References Cited

UNITED STATES PATENTS

| | | | |
|---|---|---|---|
| 3,630,204 | 12/1971 | Fishbein | 128/305 R |
| 3,633,583 | 1/1972 | Fishbein | 128/305 R |
| 3,667,456 | 6/1972 | Charnley | 128/305 R X |
| 3,702,611 | 11/1972 | Fishbein | 128/305 R |
| 3,737,984 | 6/1973 | Pietroski | 29/78 X |

*Primary Examiner*—Channing L. Pace
*Attorney, Agent, or Firm*—David A. Burge Co.

[57] ABSTRACT

A surgical milling tool includes a body having a hemispherically-shaped outer surface and defining an internal cavity. Cutting blades carried at spaced locations on the outer surface are operative to mill tissues of a joint socket when the tool is introduced and rotated in the socket. Holes are formed through the outer surface and communicate with the internal cavity to channel cut-off tissues into the cavity as the tool is rotated. A tool support is releasably connected to the tool body to assist in positioning and rotating the body. The support includes a cover which releasably closes the body cavity to retain cut-off tissues within the cavity. Several related tool body and tool support embodiments are described which include structures for releasably drivingly connecting the tool body and the tool support. Some of the embodiments include movable latching elements for securing connections formed between the tool bodies and the tool supports.

54 Claims, 62 Drawing Figures

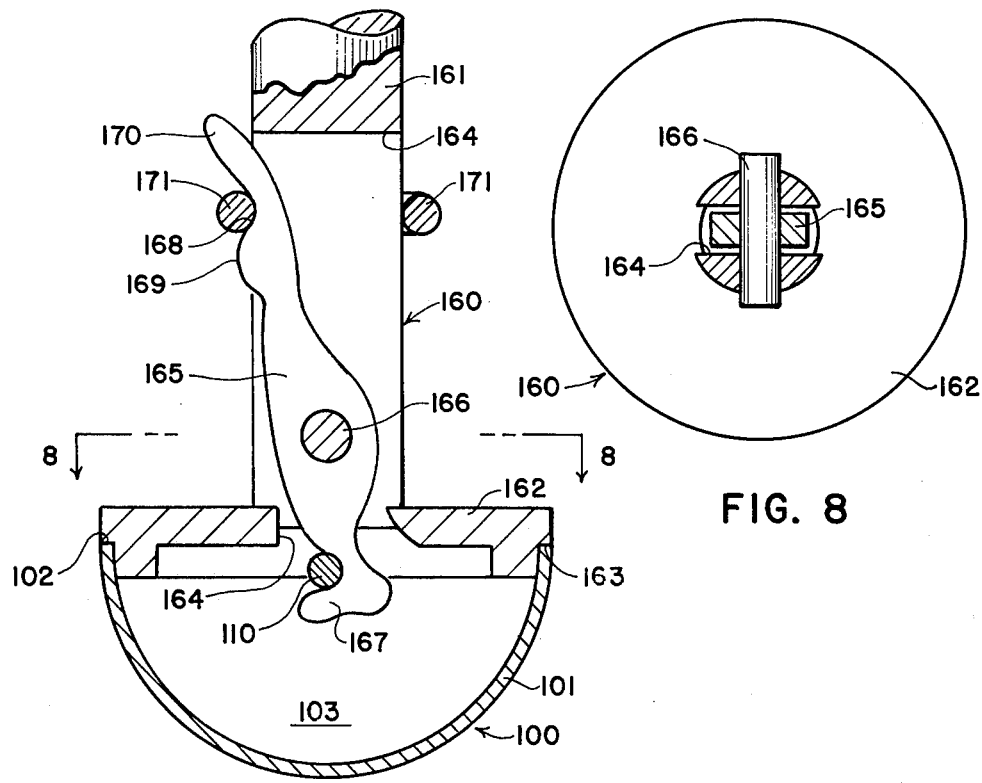
FIG. 7
FIG. 8
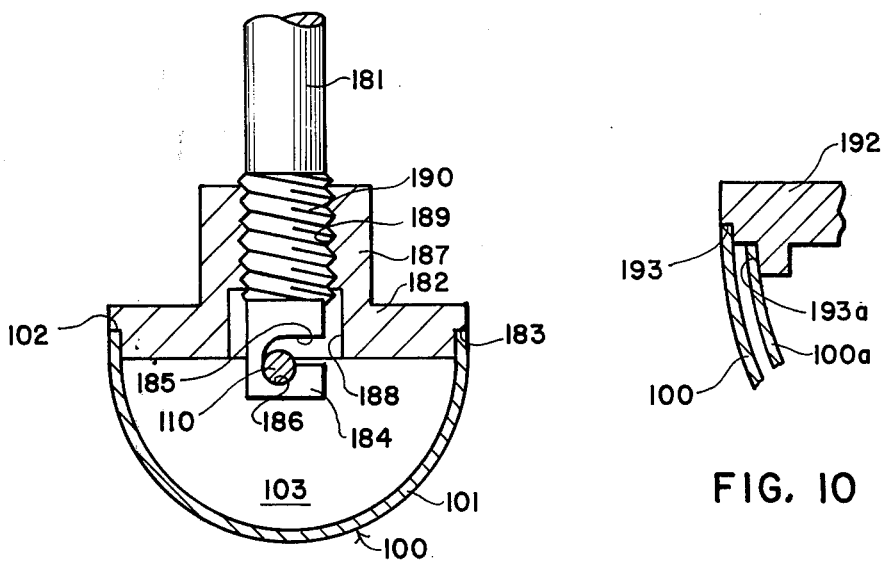
FIG. 9
FIG. 10

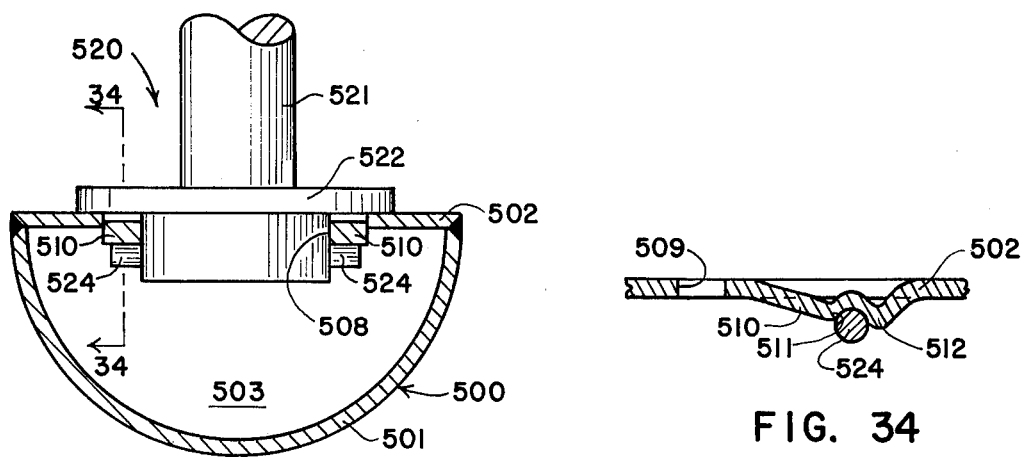
FIG. 33
FIG. 34
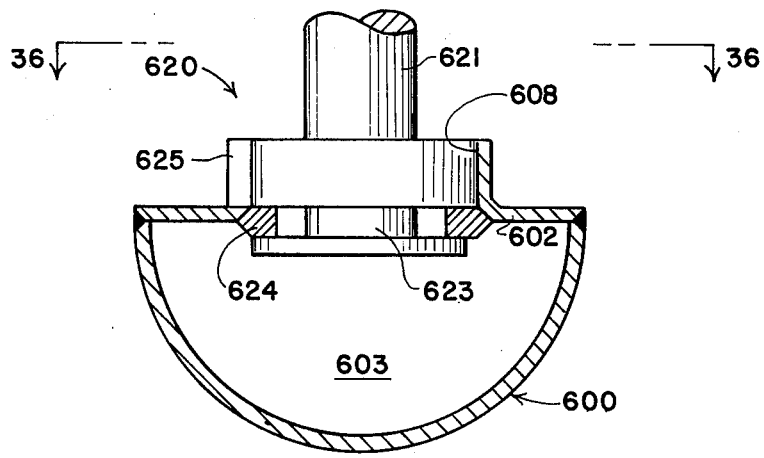
FIG. 35
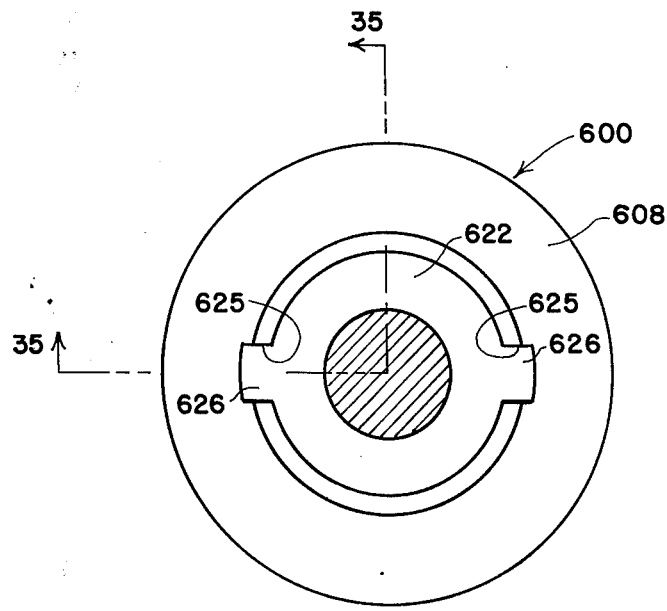
FIG. 36

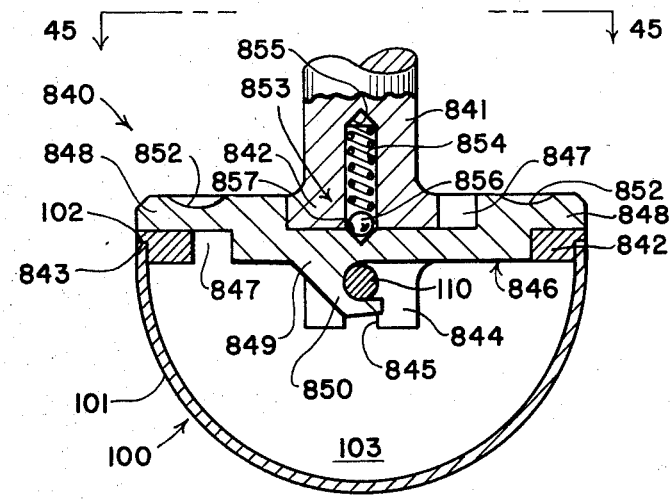
FIG. 44
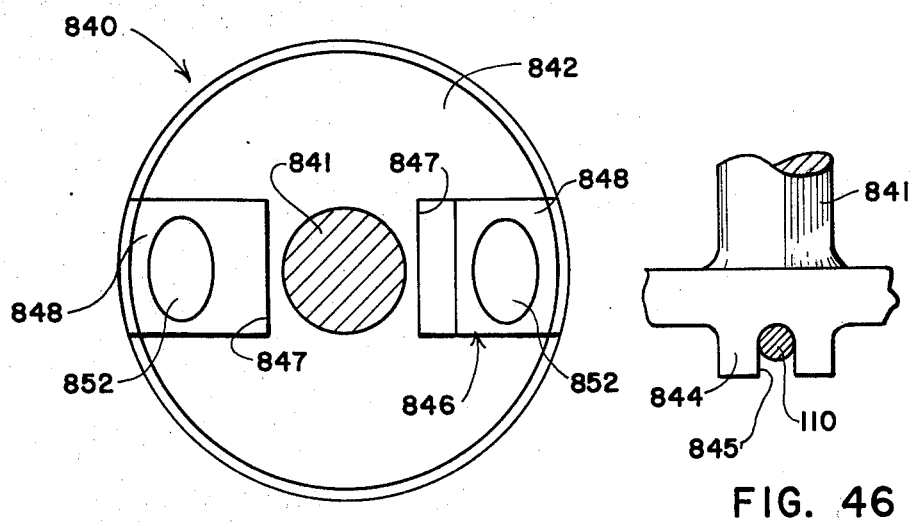
FIG. 45
FIG. 46

MILLING TOOL FOR PREPARING A JOINT SOCKET IN THE PROSTHETIC REPLACEMENT OF A JOINT

BACKGROUND OF THE INVENTION

1. Field of the Invention

The present invention relates generally to surgical apparatus and more particulary to a milling tool for the preparation of a joint socket in total prosthesis of a joint.

2 Prior Art

In the total prosthesis of joints such as a hip joint, the existing hip joint ball is removed and the hip joint socket is shaped and enlarged to receive a pre-formed artificial hip joint ball or a pre-formed artificial socket which will matingly engage an artificial hip joint ball. Proper seating of the artificial ball in the pathologically altered hip joint socket is dependent on the careful and accurate preparation of the socket.

While a hammer and chisel were the principal tools used to prepare the hip socket in early prosthesis procedures, these instruments have largely been replaced by milling tools. Milling tools reduce the time required to prepare a hip socket and facilitate the accurate shaping of the socket.

One proposed milling tool has a hemispherical tool body which is of solid construction. Milling blades of quarter-circle shape are provided on the body in a spiral arrangement. In a second proposed milling tool, several radially arranged plates form a generally hemispherically-shaped tool body. Milling blades are formed on the edges of the plates. Neither of these milling tool structures is well adapted for use in milling the several types of tissues encountered in a joint socket such as connective fatty tissues, joint cartilage, and bone tissues of differing densities. In the first proposed construction, the channels between the milling blades tend to stop up easily, while in the latter proposed construction a danger exists of breaking into aged de-limed bones.

A third proposal which represents an improvement over the described milling tools utilizes a hollow hemispherical tool body. Milling blades are formed on the body as by forming openings through the body and by sharpening selected edges of these openings. This proposed tool has been found to be acceptable for safely and expediently milling all forms of joint tissue.

A problem with all three of these proposed tools is that milled tissue material is not thoroughly collected by the tool and tends to collect in the softer tissues of the joint during milling. The milled tissue particles are not easily removed from the wound surface even with the most thorough rinsing and swabbing procedures.

Tests have shown that where ossifications have resulted in the immediate vicinity of an artificial joint, the milling residues which are left in the joint are a significant factor in their causation. Such ossifications can lead to a limitation in joint movement and even to a complete stiffening of the joint.

SUMMARY OF THE INVENTION

The present invention overcomes the foregoing and other drawbacks of the prior art and provides a novel and improved surgical milling tool.

A feature of milling tools which embody the present invention is that they facilitate the collection and retention of milled tissues and inhibit the escape of tissue residue into a joint socket both during milling and while the milling tool is being removed from the prepared joint socket.

In the preferred practice of the present invention, a hollow-bodied milling tool is used which has openings that extend from the vicinity of the milling blades and into a central cavity to channel milled tissues into the cavity. A tool support is releasably connected to the tool body and includes a cover which releasably closes the body cavity. During the milling procedure, regardless of the attitude in which the tool is positioned, the cover operates to retain milled tissues within the cavity and prevents their escape into the wound.

A releasable connection is formed between the tool support and the tool body. Interfitting or interconnectable formations are provided on the tool support and on the tool body to establish this releasable connection. The interfitting or interconnectable formations are configured to perform the dual functions of holding the tool body on the support and of drivingly connecting the body and the support so that torque can be transmitted from the support to rotate the body.

A preferred form of the tool body includes a rod which extends through the body cavity and is rigidly connected to opposite sides of the hemispherical body wall. The tool support is provided with formations which receive the body rod to retain the body on the support and to drivingly interconnect the body and the support.

Alternate forms of tool bodies and supports can be used which embody the basic aspects of the present invention. Where mating, interfitting formations are not provided on the body and the support, other types of formations which are alignable for interconnection by one or more movable connecting elements are preferably used. Latching elements may also be provided to secure a connection which has been established between a tool body and a tool support.

While several embodiments of tool bodies and tool supports are described, the embodiments each feature a releasable connection which permits facile interchanging of milling tools, easy opening of the tool cavities to discharge accumulated tissues, and a secure means of holding the tools in place on their supports.

Each of the described tool supports includes a cover which securely closes the internal cavity of a tool mounted thereon. In the preferred practice of the invention, such covers each have a circumferentially extending recess which receives the rim of a tool body. The covers preferably have an outer diameter which correspond to and do not extend significantly radially outwardly from the maximum outer diameter of their associated tool body.

It is a general object of the present invention to provide a novel and improved surgical milling tool.

Other objects and a fuller understanding of the invention may be had by referring to the following description and claims taken in conjunction with the accompanying drawings.

BRIEF DESCRIPTION OF THE DRAWINGS

FIG. 7 is a side elevational view of the tool body of FIG. 1 positioned on an alternate support structure, portions of the view being broken away and shown in cross-section to illustrate detail;

FIG. 8 is a sectional view as seen from a plane indicated by a line 8—8 in FIG. 7;

FIG. 9 is a side elevational view of the tool body of FIG. 1 positioned on an alternate support structure, the portions of the view being broken away and shown in cross-section to illustrate detail;

FIG. 10 is a cross-sectional view of a portion of the tool body of FIG. 1, and a portion of a second tool body having a smaller diameter, both of the tool bodies being carried on a support;

FIG. 33 is a side elevational view of an alternate tool body and tool support, portions of the view being broken away and shown in cross-section to illustrate detail;

FIG. 34 is an enlarged sectional view as seen from a plane indicated by a line 34—34 in FIG. 33;

FIG. 35 is a side elevational view of an alternate tool body and tool support, positions of the view being broken away and shown in cross-section to illustrate detail;

FIG. 36 is a sectional view as seen from a plane indicated by a line 36—36 in FIG. 35, the view including a broken line 35—35 indicating a broken plane from which the sectional view 35 is taken;

FIG. 44 is a side elevational view of the tool body of FIG. 1 as carried on an alternate tool support, portions of the view being broken away and shown in cross-section to illustrate detail;

FIG. 45 is a cross-sectional view as seen from a plane indicated by a line 45—45 in FIG. 44;

FIG. 46 is a side elevational view of the tool support of FIG. 45 as seen from a plane indicated by a line 46—46 in FIG. 45;

DESCRIPTION OF THE PREFERRED EMBODIMENT

Figure 1:
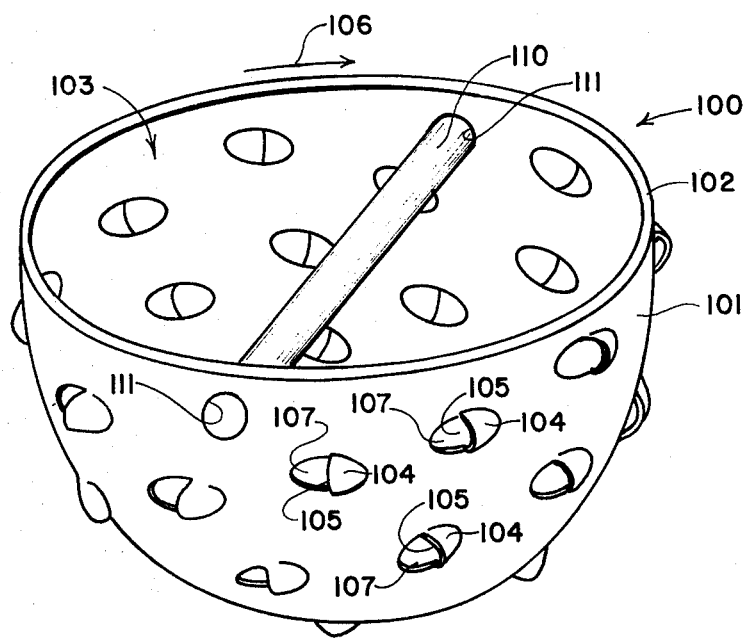
FIG. 1 is a perspective view of a milling tool body incorporating certain aspects of the present invention.

Referring to FIG. 1, a milling tool is indicated generally by the numeral 100. The tool 100 has a hollow, hemispherical body 101 which is formed from metal and has a rim 102. A central, hemispherical cavity 103 is defined within the body 101.

A plurality of outwardly extending cup-shaped projections 104 are formed integrally with the tool body 101. The projections 104 are spaced along an imaginary spiral line which extends circumferentially around the body 101.

A plurality of milling blades 105 are formed on the leading edges of the projections 104. The projections 104 all face forwardly such that when the tool 100 is rotated in a direction indicated by the arrow 106, the milling blades 105 are operative to mill tissue surfaces engaged by the tool 100.

A plurality of holes 107 are formed through the tool body 101. Each of the holes 107 is located forwardly of a separate one of the cup-shaped projections 104 adjacent a separate one of the blades 105. When the tool 100 is rotated in the direction of the arrow 106, the cup-shaped projections 104 and the holes 107 cooperate to channel such tissue as is cut off by the blades 105 into the central cavity 103.

The described milling tool 100 can be secured in a number of ways to a support structure for rotation. One preferred manner of securing the tool 100 to a support is through the utilization of a mounting rod 110 secured to the tool body 101. Two holes 111 are formed through opposite side portions of the tool body 101. The mounting rod 110 has its opposite end regions supported in the holes 111. The mounting rod 110 is secured to the tool body 101 as by a suitable means such as soldering or welding.

Figure 2:
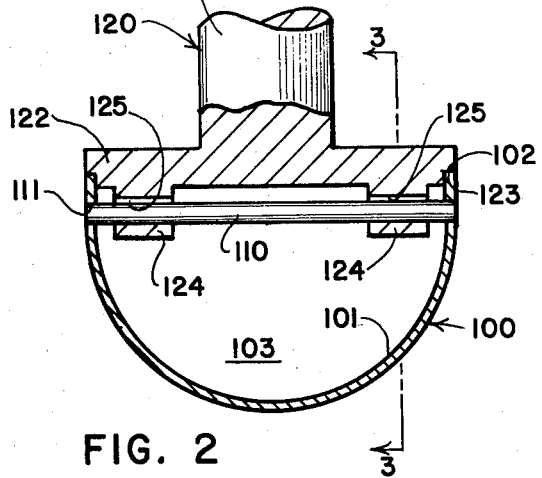
FIG. 2 is a side elevational view of the milling tool body of FIG. 1 attached to a first tool support embodiment, portions of the view being broken away and shown in cross-section to illustrate detail.
Figure 3:
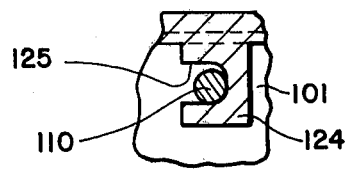
FIG. 3 is a sectional view as seen from a plane indicated by a line 3—3 in FIG 2.

Referring to FIG. 2, a tool support is indicated generally by the numeral 120. The support 120 is a one-piece structure including a shaft 121 having an enlarged diameter mounting head 122 formed integrally at one end. The head 122 has an outer diameter which is substantially the same as the outer diameter of the tool body 101. A circumferentially extending recess 123 is formed in the head 122 and is configured to receive the rim 102 of the tool body 101. A feature of the mounting head 122 is that it forms a cover which closes the open end of the tool cavity 103 to retain tissue materials within the cavity 103.

A pair of hook-shaped mounting projections 124 are formed integrally with the head 122 and depend into the cavity 103. Each of the mounting projections 124 has a notch 125 formed in it to receive the mounting rod 110.

The tool 100 is mounted on the support 120 by positioning the rim 102 in the recess 123 and by rotating the tool 100 relative to the support 120 until the mounting rod 110 is received in the notches 125. The tool 100 is removed from the support 120 to discharge such tissue material as may have accumulated in the cavity 103 by counterrotating the tool 100 relative to the support 120 to remove the rod 110 from the notches 125, whereafter the tool 100 disengaged from the support 120. The notches 125 in the hook-shaped projections 124 are oriented such that when the support 120 is driven to rotate the tool 100 in the direction of the arrow 106, the rod 110 is retained securely in the notches 125.

The tool support shaft 121 can be driven by hand or by motor to rotate the tool 100. In the preferred practice of the present invention, a pneumatic motor (not shown) is drivingly connected to the shaft 121 to rotate the tool 100 at a controlled angular velocity in the direction of the arrow 106.

Figure 4:
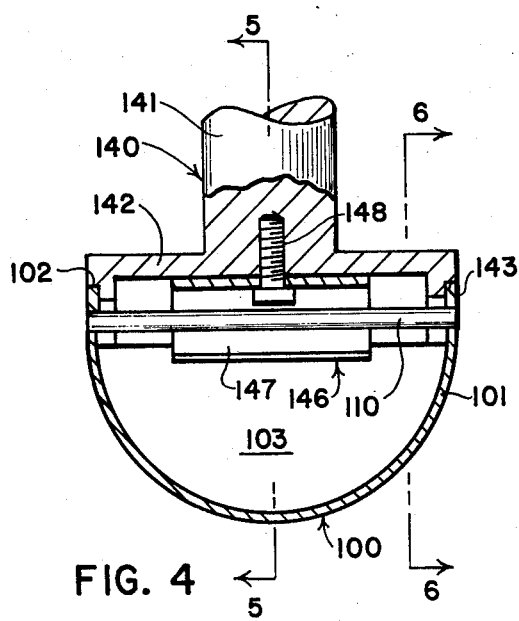
FIG. 4 is a side elevational view of the tool body of FIG. 1 supported on an alternate tool support, portions of the view being broken away and shown in cross-section to illustrate detail.
Figure 5:
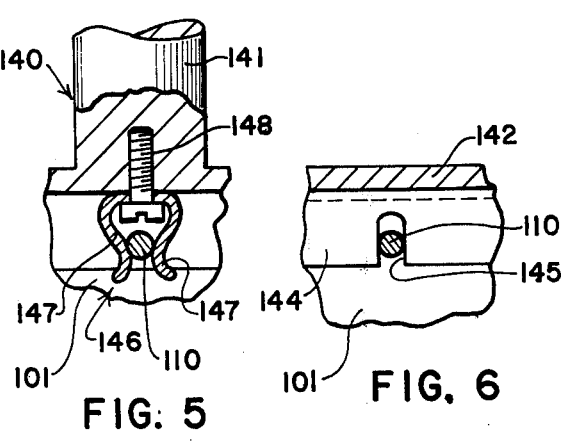
FIGS. 5 and 6 are sectional views as seen from planes indicated by lines 5—5 and 6—6 in FIG. 4.
Figure 6:
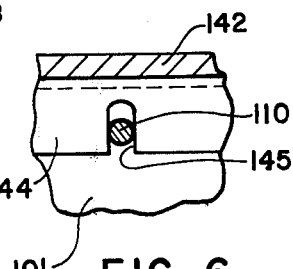

Referring to FIGS. 4–6, an alternate tool support which is usable with the milling tool 100 is indicated generally by the numeral 140. The support 140 is a three-piece structure including a shaft 141 having an enlarged diameter mounting head 142 formed integrally at one end. The head 142 has an outer diameter which is substantially the same as the outer diameter of the tool body 101. A circumferentially extending recess 143 is formed in head 142 and is configured to receive the rim 102 of the tool body 101. A feature of the mounting head 142 is that it forms a cover which closes the open end of the tool cavity 103 to retain tissue materials within the cavity 103.

An angular flange 144 is formed integrally with the mounting head 142 and depends into the cavity 103 along the inner wall of the tool 100. Referring to FIGS. 4 and 6, a pair of notches 145 are formed in opposite sides of the annular flange 144 to receive the rod 110. The notches 145 establish a driving connection between the tool 100 and the support 140 which permits the tool 100 to be rotated in response to rotation of the tool support shaft 141.

A spring member 146 is provided on the tool support 140 to retain the tool 100 in place on the support 140.

Referring to FIG. 5, the spring member 146 has an inverted U-shaped cross-section including a pair of legs 147 which are configured to grasp and releasably retain the tool rod 110. A threaded fastener 148 extends through a hole in the spring member 146 and is threaded into the support head 140 to hold the spring member 146 in place on the support head 142.

The tool 100 is mounted on the support 140 by aligning the rod 110 with the notches 145 and by exerting axial pressure on the tool 100 to snap the rod 110 into position between the spring legs 147. The tool 100 is removed from the support 140 to discharge such tissue material as may have accumulated in the cavity 103 by pulling the tool 100 axially of the support 140 to disengage the rod 110 from between the spring legs 147.

Referring to FIGS. 7, 8, an alternate tool support which is usable with the milling tool 100 is indicated generally by the numeral 160. The support 160 is a multipart assembly including a shaft 161 having an enlarged diameter mounting head 162 formed integrally at one end. The head 162 has an outer diameter which is substantially the same as the outer diameter of the tool body 101. A circumferentially extending recess 163 is formed in the head 162 and is configured to receive the rim of the tool body 101. A feature of the mounting head 162 is that it forms a cover which closes the open end of the tool cavity 103 to retain tissue materials within the cavity 103.

A slot 164 is formed through the shaft 161 and through the mounting head 162. A lever 165 is positioned in the slot 162. A pin 166 extends through aligned holes formed in the lever 165 and in the shaft 161 to pivotally mount the lever 165 in the slot 164. The lower end region of the lever 165 is provided with a hook-like portion 167 which is adapted to engage the rod 110 to clamp the tool 100 on the support 160. The upper end region of the lever 165 extends out of the slot 164 and defines a curved recess 168 located between a rounded projection 169 and a handle formation 170.

A locking ring 171 is movably carried on the tool support shaft 161 to releasably lock the lever 165 in a tool clamping position. When the hook-shaped lever portion 167 engages the tool rod 110 to clamp the tool 100 in place on the support 160, as shown in FIG. 7, the ring 171 is movable axially of the shaft 161 and over the projection 169 to engage the recess 168. The lever 165 is elastically deformable as by pushing the handle portion 170 radially toward the shaft 161 to permit the locking ring 171 to pass over the projection 169 and into the recess 168, whereafter when the handle portion 170 is released, the lever 165 will elastically reform to a configuration where the recess 168 securely engages the ring 171.

The tool 100 is mounted on the support 160 by positioning the rim 102 in the recess 163 with the axis of the tool rod 110 extending parallel to the axis of the pin 166. The lever 165 is then pivoted clockwise, as viewed in FIG. 7, to bring the hook-shaped portion 167 into engagement with the rod 110. The handle portion 170 is then pressed radially inward toward the shaft 161 while the locking ring 171 is moved axially upwardly along the shaft 161 over the projection 169 and into alignment with the recess 168. The handle portion 170 is then released whereby the handle 165 elastically deforms to engage the locking ring 171 and retain the locking ring 171 in the recess 168. The tool 100 is removed from the support 160 to discharge such tissue as may have accumulated in the cavity 103 by reversing these steps.

Referring to FIG. 9, still another tool support which is usable with the milling tool 100 is indicated generally by the numeral 180. The tool support 180 is a two-piece structure including a shaft 181 and a separate enlarged diameter mounting head 182 which is carried on the shaft 181. The head 182 has another diameter which is substantially the same as the outer diameter of the tool body 101. A circumferentially extending recess 183 is formed in the head 182 and is configured to receive the rim 102 of the tool body 101. A feature of the mounting head 182 is that it forms a cover which closes the open end of the tool cavity 103 to retain tissue materials within the cavity 103.

A hook-shaped formation 184 is provided on the lower end region of the shaft 184. The hook-shaped formation 184 includes a notch 185 which is adapted to receive the tool rod 110. An axially downwardly extending depression 186 is formed near the inner end of the notch 186 to receive and seat the tool rod 110.

A central upstanding hub 187 is formed integrally with the mounting head 182. A hole 188 is formed through the hub 187 to receive the shaft 181. The lower end region of the hole 188 is a smooth walled bore which surrounds the hook-shaped formation 184. The upper end region of the hole is provided with internal threads 189.

External threads 190 are formed on the shaft 181. The external threads 190 engage the internal threads 189 to form a connection between the shaft 181 and the mounting head 182. When the head 182 is rotated in one direction relative to the shaft 181, the head 182 moves upwardly along the shaft 181. When the head 182 is rotated in the opposite direction relative to the shaft 181, the head 182 moves downwardly along the shaft.

The tool 100 is mounted on the support 180 by rotating the mounting head 182 to move it upwardly along the shaft 181 to a position where the tool rod 110 can be moved into the slot 185 without causing the tool 100 to contact the mounting head 182. Once the tool rod 110 has been seated in the depression 186, the mounting head 182 is rotated in the opposite direction to move it downwardly along the shaft 181 to a position where the rim 102 is seated in the recess 183. Removing the tool 100 from the support 180 to discharge such tissue as has accumulated in the cavity 103 is effected by reversing these steps.

The described mounting heads 122, 142, 162, 182 can be provided with a stepped arrangement of circumferentially extending recesses to receive and mount milling tools of different diameters. Referring to FIG. 10, a portion of a mounting head 192 has a stepped arrangement of two circumferentially extending recesses 193, 193a of different diameters to alternatively receive the rims of the milling tool 100 or of a smaller diameter milling tool 100a. Regardless of which diameter milling tool 100, 100a is used with the mounting head 192, the mounting head 192 serves as a cover to close the open end of the tool cavity.

Figure 11:
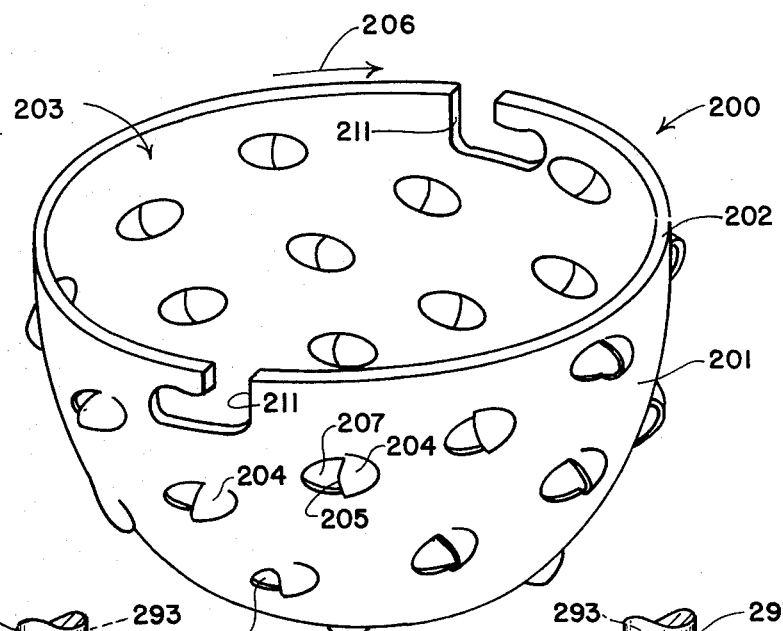
FIG. 11 is a perspective view of an alternate tool body embodying certain features of the present invention.

Referring to FIG. 11, an alternate milling tool embodiment is indicated generally by the numeral 200. The tool 200 is constructed the same as the tool 100 in its provision of a hollow body 201 which has a rim 202 and which defines a cavity 203, in its provision of cup-shaped projections 204 arranged in a spiral line around the body 201, in its provision of milling blades 205 on the projections 204, and in its provision of holes 207 located forwardly of the projections 204. When the tool 200 is rotated in the direction of arrow 206, the cup-shaped projections 204 and the holes 207 cooperate to channel such tissue as is cut off by the blades 205 into the central cavity 203.

In order to secure the tool 200 to a support structure for rotation, two hook-shaped slots 211 are formed in opposite sides of the tool 200. The slots 211 open through the rim 202 and extend for a relatively short distance generally perpendicular to the rim 202, whereafter the slots turn and extend for a relatively long distance circumferentially of the tool 200 in the direction of the arrow 206.

Figure 12:
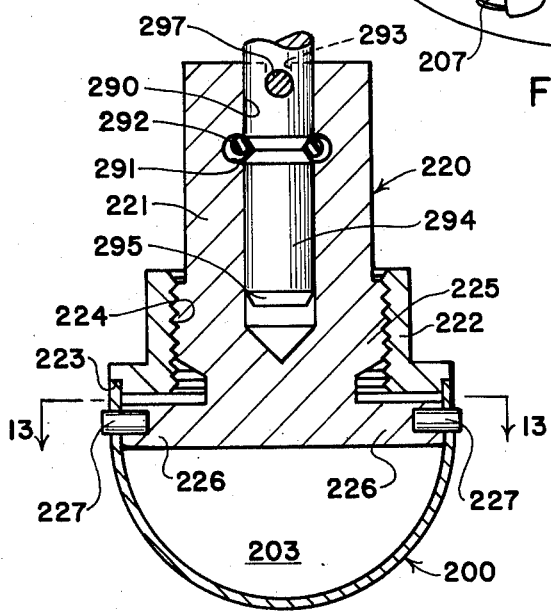
FIG. 12 is a sectional view of the tool body of FIG. 11 carried on an alternate support.

Referring to FIG. 12, a tool support is indicated generally by the numeral 220. The support 220 includes a hub 221 and a separately formed annular mounting head 222 which surrounds a portion of the hub 221. The head 222 has an outer diameter which is substantially the same as the outer diameter of the tool body 201. A circumferentially extending recess 223 is formed in the head 222 and is configured to receive the rim 202 of the tool body 201. A feature of the mounting head 222 is that it forms a cover which closes the open end of the tool cavity 203 to retain tissue materials within the cavity 203.

A threaded connection is formed between the hub 221 and the mounting head 222. An internally threaded hole 224 is formed axially through the hub 222. External threads 225 are formed on the hub 221 and engage the internal threads in the hole 224. When the head 222 is rotated in one direction relative to the hub 221, the head 222 moves upwardly along the hub 221. When the head 222 is rotated in the opposite direction relative to the hub 221, the head 222 moves downwardly along the hub 221.

Figure 13:
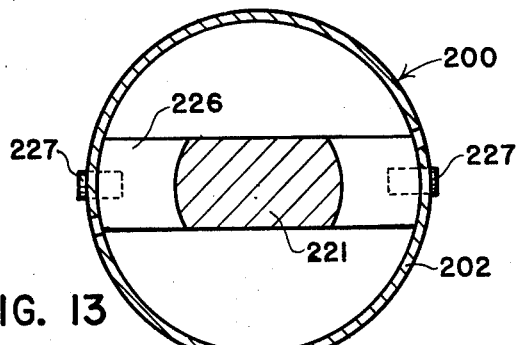
FIG. 13 is a sectional view as seen from a plane indicated by a line 13—13 in FIG. 12.

Referring to FIGS. 12 and 13, a pair of radially extending projections 226 are formed integrally with the hub 221. A pair of radially extending pins 227 are rigidly carried by the projections 226. As is shown in FIG. 14, the pins 227 have diameters which permit their positioning in the slots 211.

Figure 14:
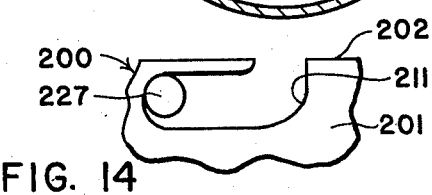
FIG. 14 is an enlarged side elevational view of a portion of the tool body and tool support shown in FIG. 12.

The tool 200 is mounted on the support 220 by rotating the mounting head 222 to move it upwardly along the hub 221 to a position where the radially extending pins 227 can be inserted as shown in FIG. 14 in the slots 211. Once the pins 227 are seated in the ends of the slots 211, the mounting head 222 is rotated in the opposite direction to move it downwardly along the hub 221 to a position where the rim 202 is seated in the recess 223. As the head 222 moves downwardly along the hub 221, it comes into clamping engagement with the tool 200 and establishes a rigid connection between the tool 200 and the hub 221. Removing the tool 200 from the support 220 to discharge such tissue as has accumulated in the cavity 203 is effected by reversing these steps.

Figure 16:
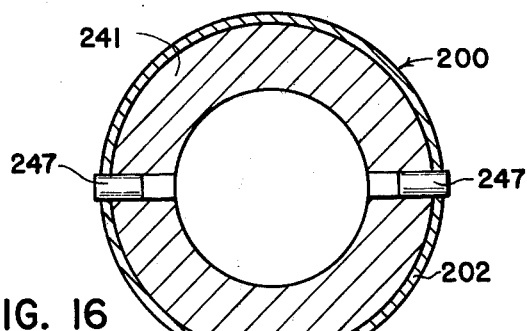
FIG. 16 is a sectional view as seen from a plane indicated by a line 16—16 in FIG. 15.
Figure 17:
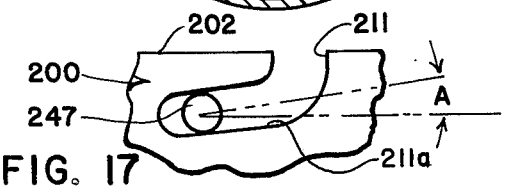
FIG. 17 is an enlarged side elevational view of a portion of the tool body and tool support shown in FIG. 15.

Referring to FIG. 17, a modification can be made in the orientation of the tool slots such that circumferentially extending portions 211a of the slots 211 are inclined at an angle "A" relative to the plane of the tool rim 202. Where the tool 200 is modified as shown in FIG. 17, an alternate tool support of the type shown in FIGS. 15, 16 is preferably used.

Figure 15:
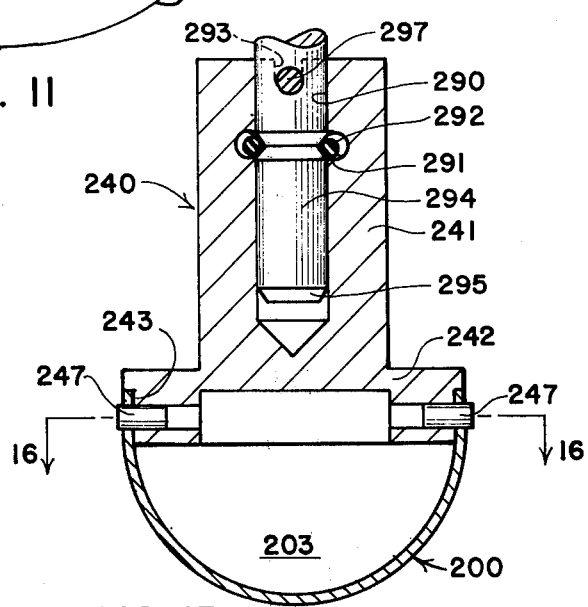
FIG. 15 is a sectional view of the tool of FIG. 11 carried on an alternate support.

Referring to FIGS. 15 and 16, a tool support is indicated generally by the numeral 240. The support 240 includes a hub 241 which has an enlarged diameter mounting head formed integrally at one end. The head 242 has an outer diameter which is substantially the same as the outer diameter of the tool body 201. A circumferentially extending recess 243 is formed in the head 242 and is configured to receive the rim 202 of the tool body 201. A feature of the mounting head 242 is that it forms a cover which closes the open end of the tool cavity 203 to retain tissue materials within the cavity 203.

A pair of radially extending pins 247 are rigidly carried by the mounting head 242. As is shown in FIG. 17, the pins 247 have diameters which permit their positioning in the slots 211.

The tool 200, modified as shown in FIG. 17, is mounted on the support 240 by relatively axially moving the tool 200 and the support 240 to position the pins 247 in the axially extending portions of the slots 211. The tool 200 is then rotated relative to the support 240 to move the pins 247 into the inclined circumferentially extending portions 211a of the slots 211. The slots 211 are configured such that when the pins 247 reach approximately the position shown in FIG. 17, the top surfaces of the pins 247 engage the upper walls of the slot portions 211a to clamp the tool rim 202 into engagement with the recess 243. The angle "A" is preferably quite small and is selected to have a magnitude sufficient to effect the desired clamping without providing an angle that will cause the tool 200 to unintentionally loosen from engagement with the support 240. Removing the tool 200 from the support 240 to discharge such tissue as has accumulated in the cavity 203 is effected by reversing these steps.

Figure 21:
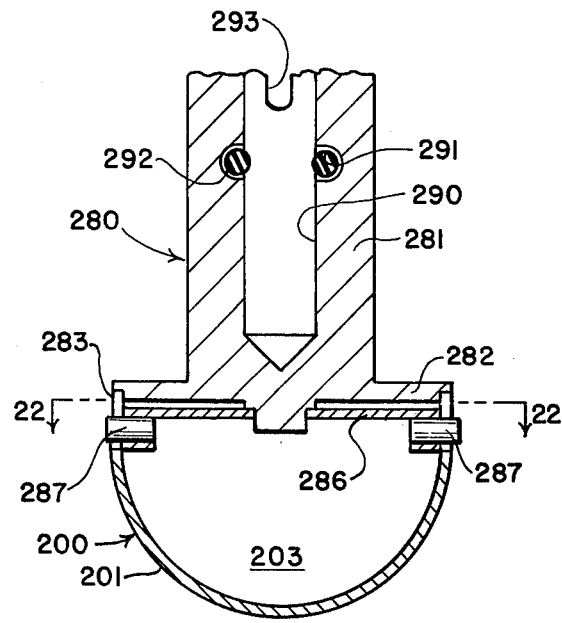
FIG. 21 is a sectional view of the tool body of FIG. 11 carried on an alternate support.
Figure 19:
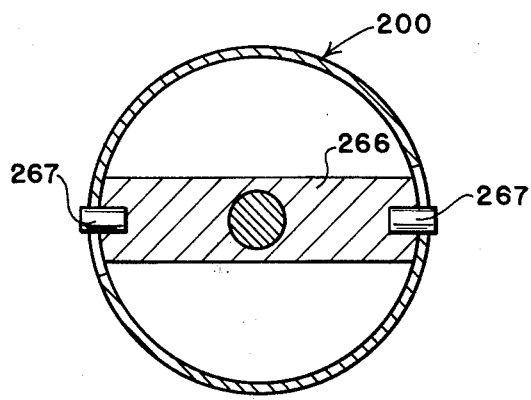
FIG. 19 is a sectional view as seen from a plane indicated by a line 19—19 in FIG. 18.
Figure 22:
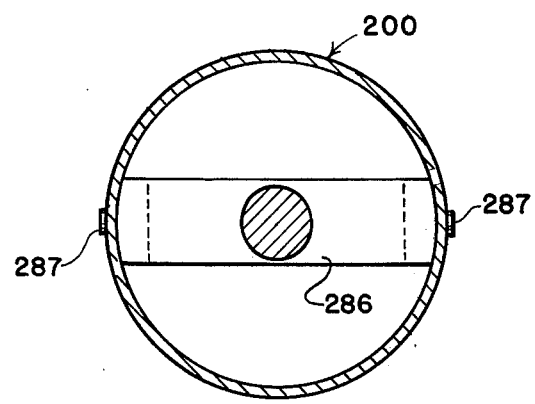
FIG. 22 is a sectional view as seen from a plane indicated by a line 22—22 in FIG. 21.
Figure 20:
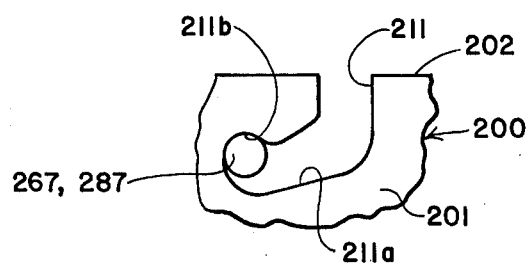
FIG. 20 is an enlarged side elevational view of a portion of the tool body and tool support shown in FIG. 18.

Referring to FIG. 20, still another modification can be made in the configuration of the tool slots 211 to provide the end regions of the slots 211 with upwardly extending depressions 211b at the ends of inclined circumferentially extending portions 211a. Where the tool 200 is modified as shown in FIG. 20, either a tool support embodiment such as is shown in FIGS. 18, 19 or an embodiment such as is shown in FIGS. 21, 22 is preferably used.

Figure 18:
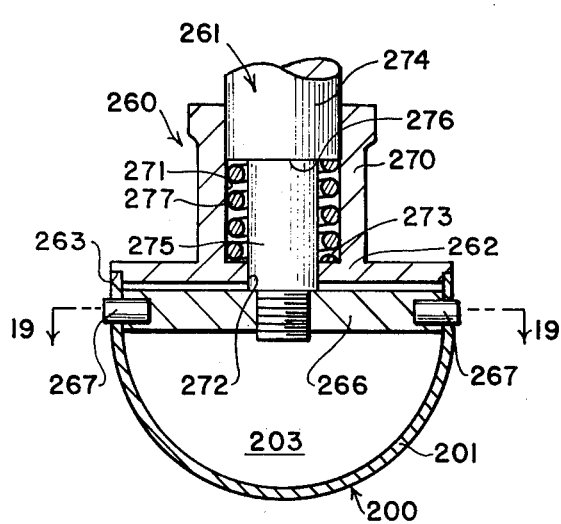
FIG. 18 is a sectional view of the tool body of FIG. 11 as carried on an alternate support.

Referring to FIGS. 18 and 19, a tool support is indicated generally by the numeral 260. The support 260 includes a shaft 261 and a separately formed mounting head 262 positioned around the shaft 261. The head 262 has an outer diameter which is substantially the same as the outer diameter of the tool body 201. A circumferentially extending recess 263 is formed in the head 262 and is configured to receive the rim 202 of the tool body 201. A feature of the mounting head 262 is that it forms a cover which closes the open end of the tool cavity 203 to retain tissue materials within the cavity 203.

A radially extending member 266 is rigidly secured to the lower end region of the shaft 261. A pair of radially extending pins 267 are rigidly carried by the member 266. The pins 267 have diameters which permit the pins 267 to be positioned in the slots 211.

The mounting head 262 has an upstanding annular hub portion 270. An axially extending hole having a stepped bore with upper and lower end regions 271, 272 is formed through the hub portion 270. A radially extending shoulder 273 joins the end regions 271, 272.

The shaft 261 has a relatively large diameter portion 274 which slip fits within the upper end region 271, and a reduced diameter portion 275 which slip fits within the lower end region 272. A radially extending shoulder 276 joins the shaft portions 274, 275.

A compression coil spring 277 is positioned in the upper end region 271 and surrounds the shaft portion 275. Opposite end regions of the spring 277 engage the shoulders 273, 276. The spring 277 biases the mounting head 262 downwardly along the shaft 261 toward the radially extending member 266.

The tool 200, modified as shown in FIG. 20, is mounted on the support 260 by relatively axially moving the tool 200 and the support 260 to position the pins 267 in the axially extending portions of the slots 211. The tool 200 is then rotated relative to the support 260 to move the pins 267 into the inclined circumferentially extending portions 211a of the slots 211. As the pins 267 move along the inclined portions 211a, the rim 202 engages the recess 263 and causes the head 262 to move upwardly along the shaft 261 in opposition to the spring 277. When the pins 267 reach the ends of the slots 211, they seat in the depressions 211b and are retained in the depressions by the biasing action of the spring 277. Removing the tool 200 from the support 260 to discharge such tissue as has accumulated in the cavity 203 is effected by reversing these steps.

Referring to FIGS. 21, 22, an alternate tool support which is usable with the tool 200, modified as shown in FIG. 20, is indicated generally by the numeral 280. The support 280 includes a hub 281 which has an enlarged diameter mounting head 282 formed integrally at one end. The head 282 has an outer diameter which is substantially the same as the outer diameter of the tool body 201. A circumferentially extending recess 283 is formed in the head 282 and is configured to receive the rim 202 of the tool body 201. A feature of the mounting head 282 is that it forms a cover which closes the open end of the tool cavity 203 to retain tissue materials within the cavity 203.

A radially extending member 286 is rigidly secured to the lower end region of the hub 281. The member 286 is relatively stiff in circumferential directions and is used to transmit driving torque to the tool 200. The member 286 is resilient in axial directions and tends to assume a flat configuration. Opposite ends of the member 286 can be deflected downwardly whereupon the resilient nature of the member 286 tends to bias the deflected ends upwardly.

A pair of radially extending pins 287 are rigidly carried on opposite end regions of the member 286. The pins 287 have diameters which permit the pins 287 to be positioned in the slots 211.

The tool 200, modified as shown in FIG. 20, is mounted on the support 280 by relatively axially moving the tool 200 and the support 280 to position the pins 287 in the axially extending portions of the slots 211. The tool 200 is then rotated relative to the support 280 to move the pins 287 into the inclined circumferentially extending portions 211a of the slots 211. As the pins 287 move along the inclined portions 211a, the rim 202 engages the recess 283 and opposite ends of the member 286 are caused to deflect downwardly. When the pins 287 reach the ends of the slots 211, they seat in the depressions 211b and are retained in the depressions 211b by the biasing action of the member 286. Removing the tool 200 from the support 280 to discharge such tissue as has accumulated in the cavity 203 is effected by reversing these steps.

The described tool supports 220, 240, 260, 280 can, of course, be provided with more than two radially extending pins 227, 247, 267, 287 for cooperation with a corresponding number of slots 211 formed in the tool 200.

The hubs 221, 241 and 281 are configured for quick connection and disconnection to a drive shaft. Referring to FIGS. 12, 15 and 21, each of the hubs 221, 241, 281 has an axially extending bore 290. An enlarged diameter groove 291 is formed in the wall of each of the bores 290. A resilient ring 292 is carried in each of the grooves 291. The rings 292 have inner diameters which are normally less than the inner diameters of their respective bores 290. The rings 292 are resiliently expansible to permit an enlargement of their inner diameters. A pair of aligned, radially extending slots 293 are formed in the upper end of the hubs 221, 241, 281.

A drive shaft 294 is provided for connection to the hubs 221, 241, 281. The shafts 294 have diameters which permit their slip fitting within the bores 290. The shafts 294 have tapered lower end regions 295 which operate to expand the inner diameters of the resilient rings 292 as the shafts 294 are inserted into the bores. A circumferentially extending groove 296 is formed on each of the shafts 294 to receive the resilient rings 292 once the shafts 294 have been inserted into the bores 290. Once the resilient rings 292 have contacted and are seated in the shaft grooves 296, the rings 292 operate to releasably retain the hubs 221, 241, 281 on the shafts 294.

A drive pin 297 extends radially through each of the shafts 294. Opposite ends of the pins 297 project radially from their shafts 294 and are adapted to drivingly engage the slots 293 when the resilient members 292 are received in the grooves 296. By this arrangement, the shafts 294 can be readily connected and disconnected from the hubs 221, 241, 281 to permit the changing of milling tools without opening any of the tool cavities 203.

Figure 23:
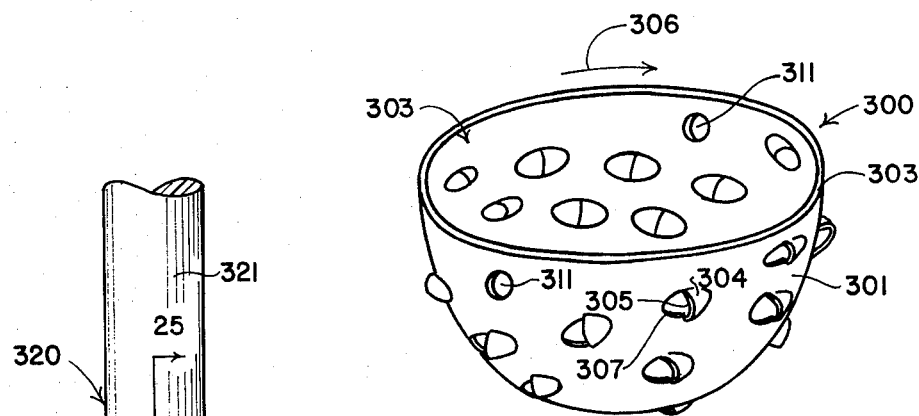
FIG. 23 is a perspective view of an alternate tool body embodiment incorporating certain aspects of the present invention.

Referring to FIG. 23, an alternate milling tool embodiment is indicated generally by the numeral 300. The tool 300 is constructed the same as the tool 100 in its provision of a hollow body 301 which has a rim 302 and which defines a cavity 303, in its provision of cup-shaped projections 304 arranged in a spiral line around the body 301, in its provision of milling blades 305 on the projections 304, and in its provision of holes 307 located forwardly of the projections 304. When the tool 300 is rotated in the direction of arrow 306, the cup-shaped projections 304 and the holes 307 cooperate to channel such tissue as is cut off by the blades 305 into the central cavity 303.

In order to secure the tool 300 to a support structure for rotation, two holes 311 are formed in opposite sides of the tool 300. The holes 311 extend radially of the tool 300 at locations spaced a short distance below the rim 302.

Figure 24:
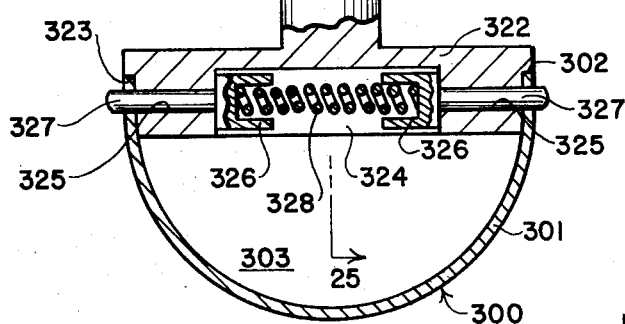
FIG. 24 is a side elevational view of the tool body of FIG. 23 as supported on an alternate support, portions of the view being broken away and shown in cross-section to illustrate detail.
Figure 25:
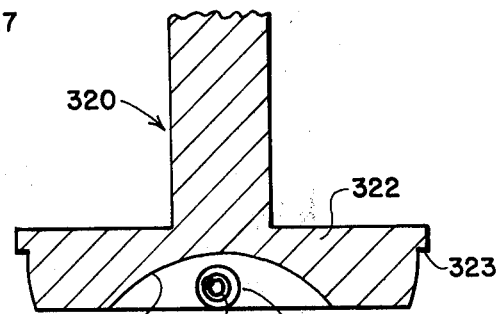
FIG. 25 is a sectional view as seen from a plane indicated by a line 25—25 in FIG. 24.

Referring to FIGS. 24 and 25, a tool support which can be used with the tool 300 is indicated generally by the numeral 320. The support 320 includes a shaft 321 having an enlarged diameter mounting head 322 formed integrally at one end of the shaft 321. The head 322 has an outer diameter which is substantially the same as the outer diameter of the tool body 301. A circumferentially extending recess 323 is formed in the head 322 and is configured to receive the rim 302 of the tool body 301. A feature of the mounting head 322 is that it forms a cover which closes the open end of the tool cavity 303 to retain tissue materials within the cavity 303.

A downwardly opening cavity 324 is formed centrally in the mounting head 322. A pair of aligned holes 325 are formed in the mounting head 322 and extend radially outwardly from the cavity 324. A pair of headed pins 327 are slidably carried in the holes 325. The pins 327 have hollow heads 326 positioned in the cavity 324. The heads 326 are engagable with walls of the cavity 324 to limit their radially outward movement. When the heads 326 engage the cavity walls, the opposite ends of the pins 327 project beyond the outer ends of the holes 325 for engagement with the tool holes 311.

A compression coil spring 328 is positioned in the cavity 324. Opposite ends of the spring 328 extend into the hollow pin heads 326 and bias the pins 327 radially outwardly toward positions where the pin heads 326 engage the walls of the cavity 324.

The tool 300 is mounted on the support 320 by depressing the outer ends of the pins 327 into the holes 325 to permit the rim 302 of the tool body 301 to pass by the holes 325. The tool 300 is then moved axially over the lower end of the mounting head 322 to bring the tool rim 302 into engagement with the recess 323. The tool 300 is then rotated relative to the support 320 as may be required to align the holes 311 with the holes 325. Once the holes 311, 325 are aligned, the pins 327 will move outwardly to engage the hole 311 in response to the biasing action of the spring 328. Removing the tool 300 from the support 320 to discharge such tissue as has accumulated in the cavity 303 is effected by depressing the pins 327 to permit axial movement of the tool 300 off the mounting head 322.

Figure 26:
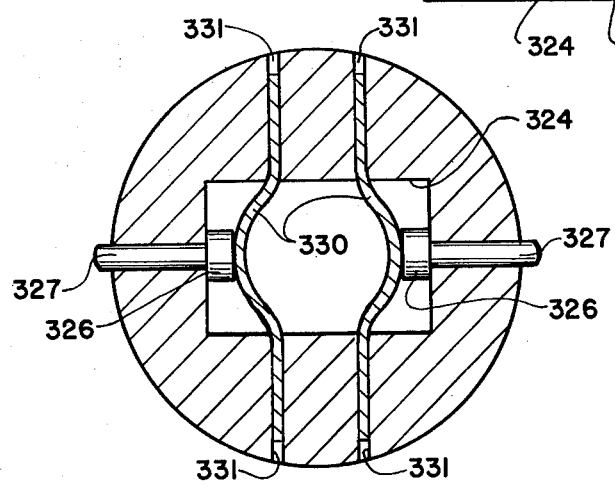
FIG. 26 is a cross-sectional view of portions of an alternate tool support.

Referring to FIG. 26, a modified form of the tool support 320 has a pair of leaf springs 330 substituted for the compression coil spring 328. Slots 331 are formed in the head 322 to receive and support opposite ends of the leaf springs 330. Central portions of the springs 330 are deformable and engage the pin heads 326 to bias the pins 327 radially outwardly.

Figure 27:
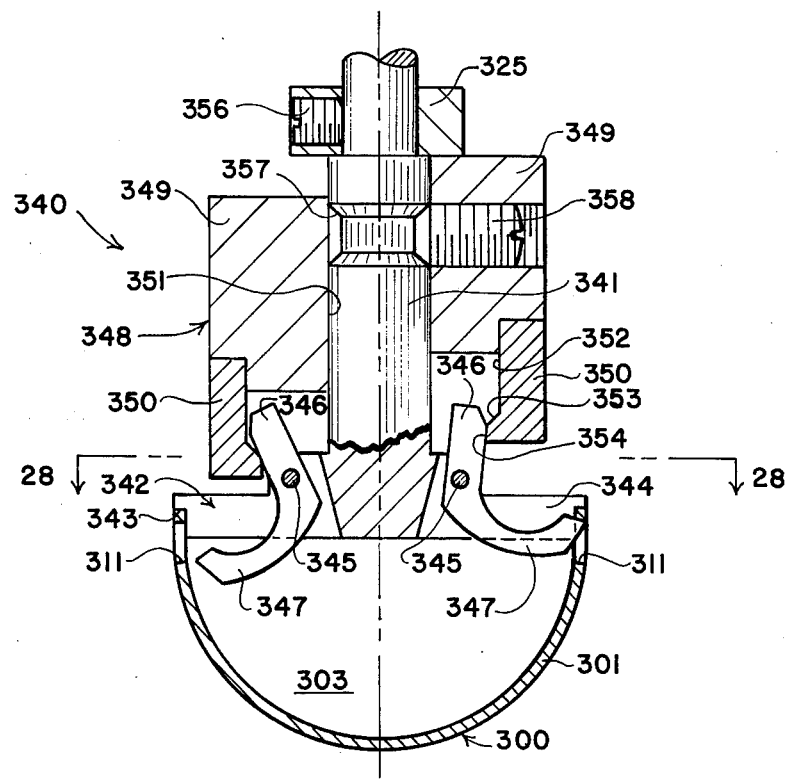
FIG. 27 is a side elevational view of the tool body of FIG. 23 carried on an alternate support, the left end right side portions of the view showing portions of the support in different positions, portions of the view being broken away and shown in cross-section to illustrate detail.

Referring to FIG. 27, an alternate tool support which is usable with the tool 300 is indicated generally by the numeral 340. The support 340 includes a shaft 341 having an enlarged diameter mounting head 342 formed integrally on the lower end region of the shaft 341. The head 342 has an outer diameter which is substantially the same as the outer diameter of the tool body 301. A circumferentially extending recess 343 is formed in the head 342 and is configured to receive the rim 302 of the tool body 301. A feature of the mounting head 342 is that it forms a cover which closes the open end of the tool cavity 303 to retain tissue materials within the cavity 303.

Figure 28:
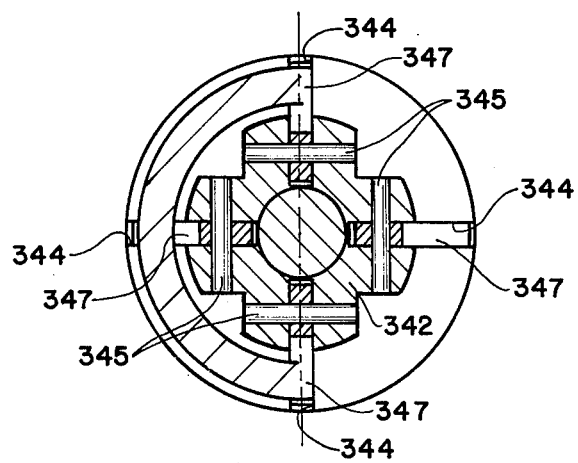
FIG. 28 is a sectional view as seen from a plane indicated by a line 28—28 in FIG. 27.

In the embodiment of FIG. 27, two pivotally mounted levers 347 are shown which are engageable with the tool holes 311. The tool support 340 may, however, be provided with more than two of the levers 347, so long as an equal number of properly spaced holes 311 are formed in the tool 300. In FIG. 28, four levers 347 are shown.

Referring to FIGS. 27 and 28, radially extending slots 344 are formed in the head 342 to loosely receive the levers 347. Pins 345 extend through aligned holes in the levers 347 and the head 342 to pivotally mount the levers 347. Each of the levers 347 is of L-shaped configuration and has an upwardly extending leg portion 346.

An axially movable sleeve assembly 348 is provided on the shaft 341 to engage the leg portions 346 and position the levers 347. The sleeve assembly 348 includes an upper sleeve member 349 and a lower sleeve member 350. The sleeve members 349, 350 are rigidly connected for concurrent axial movement between down and up positions shown respectively in the left and right side portions of FIG. 27.

A hole 351 is formed through the upper sleeve member 349 to slidably receive the shaft 341. The lower sleeve member 350 has an inner wall 352 which extends cylindrically downwardly from the upper member 349 and which then tapers inwardly as indicated at 353 to define a reduced diameter opening 354. The lever leg portions 346 extend through the opening 354 and engage the inner wall of the lower sleeve portion 350. When the sleeve assembly 348 is in its downward position as shown in the left side of FIG. 27, the lever legs 346 engage the cylindrical inner wall portion 352.

A collar 355 is positioned on the shaft 341 above the sleeve assembly 348. A setscrew 356 secures the collar to the shaft 341, thereby enabling the collar 355 to act as a stop to limit axially upward travel of the sleeve assembly 348. When the sleeve assembly 348 is in its upward position, as shown in the right side of FIG. 27, the upper sleeve member 349 engages the collar 355, and the lever legs 346 engage portions of the lower sleeve member 350 which define the reduced diameter opening 354.

A circumferentially extending groove 357 is formed in the portion of the shaft 341 which extends through the hole 351. A setscrew 358 is carried by the upper sleeve member 349 for engaging the groove 357 to releasably retain the sleeve assembly 348 in its upward position.

The tool 300 is mounted on the support 340 by loosening the setscrew 358 to release it from the groove 357 to permit movement of the sleeve assembly 348 to its downward position. As the sleeve assembly moves to its downward position, the influence of gravitational forces acting on the levers 347 will pivot the levers 347 to a position where the leg portions 346 engage the inner wall portion 350. With the lever 347 in this position, the tool 300 is positioned with its rim 302 engaging the recess 343 and with its holes 311 aligned with the levers 347. The sleeve assembly 348 is then moved to its upward position, where upon engagement between the lower sleeve member 350 and the leg portions 346 causes the legs 347 to pivot outwardly and into the holes 311. The setscrew 358 is then tightened to lock the sleeve assembly 348 in a position which securely mounts the tool 300 on the support 340. The levers 347 are preferably sufficiently resilient such that when the setscrew 358 is seated in the shaft groove 357, the levers bias the tool rim 302 into firm engagement with the head 342. Removing the tool 300 from the support 340 to discharge such tissue as has accumulated in the cavity 303 is effected by reversing these steps.

Figure 29:
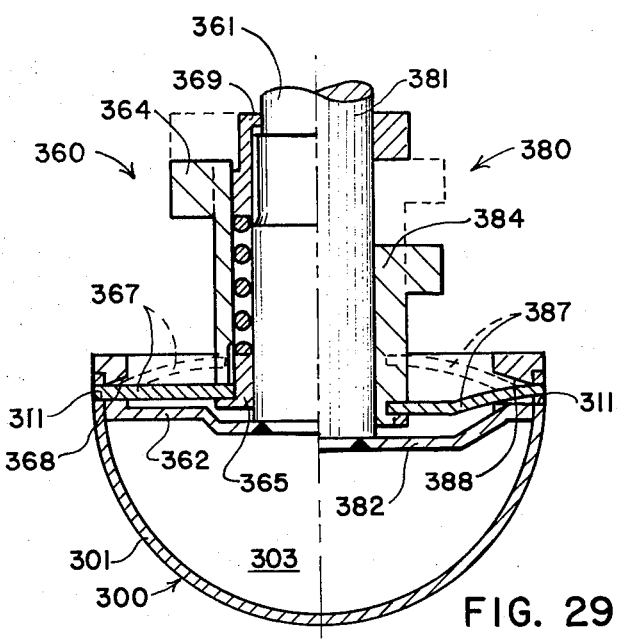
FIG. 29 is a side elevational view of a slightly modified form of the tool body of FIG. 23 supported on two slightly different support structures, one being shown in the left side of FIG. 29 and the other being shown in the right side of FIG. 29, portions of the view being broken away and shown in cross-section to illustrate detail.

Referring to FIG. 29, two alternate forms of tool supports indicated generally by the numerals 360, 380 are shown respectively in the left and right sides of the FIGURE. The supports 360, 380 are usable with the tool 300 but the tool 300 is preferably modified to include an increased number of circumferentially spaced mounting holes 311.

The tool supports 360, 380 include shafts 361, 381 which carry enlarged diameter mounting heads 362, 382 on the lower ends of the shafts 361, 381. The heads 362, 382 have outer diameters which are substantially the same as the outer diameter of the tool body 301. Circumferentially extending recesses 363, 383 are formed in the heads 362, 382 to receive the rim 302 of the tool body 301. A feature of each of the mounting heads 362, 382 is that it forms a cover which closes the open end of the tool cavity 303 to retain tissue materials within the cavity 303.

The supports 360, 380 each include a sleeve 364, 384 positioned around their shafts 361, 381. The sleeve 364 has a ring member 365 pressed into its lower end. The ring member 365 and the sleeve 384 have inner diameters which slip fit on the shafts 361, 381.

Radially extending blade springs 367, 387 are carried in cantilever fashion near the lower ends of the sleeves 364, 384. The blade springs 367, 387 project radially outwardly from the sleeves 364, 384 and extend through holes 368, 388 in the heads 362, 382 for engagement with the tool mounting holes 311.

The sleeves 364, 384 are movable between downward positions shown in solid lines in FIG. 29 and upward positions shown in phantom. When the sleeves 364, 384 are in their downward positions, the blade springs 367, 387 extend into the tool mounting holes 311 to hold the tool 300 on the heads 362, 382. When the sleeves 364, 384 are in their upward positions, the blade springs are retracted from the tool mounting holes 311 and permit the tool 300 to be removed from the heads 362, 382.

The supports 360, 380 each include a collar 369, 389 which is positioned on and secured to an associated one of the shafts 361, 381. The collar 369 depends inside the bore of the sleeve 364 and engages one end of a compression coil spring 370. The other end of the compression coil spring 370 engages the sleeve ring 365 and biases the sleeve 364 towards its downward position. The collar 389 serves as a stop which abuts the upper end of the collar 384 when the collar 384 is in its upward position. The blade springs 387 provide the necessary biasing action to normally retain the sleeve 384 in its downward position.

The tool 300 is mounted on either of the supports 360, 380 by first moving the associated sleeve 364, 384 to its upward position to radially retract the ends of the blade springs 367, 387, whereafter the tool 300 is positioned with its mounting holes 311 aligned to receive the blade springs 367, 387. The associated sleeve 364, 384 is then released to permit its return to its downward position where the blade springs 367, 387 engage the tool mounting holes 311. Removal of the tool 300 from the heads 362, 382 is effected by again moving the sleeves 364, 384 to withdraw the blade springs 367, 387.

An advantage of the tool support embodiments 360, 380 is that the tool cavity 303 is completely closed by the heads 362, 382 and none of the parts which establish connection between the tool 300 and the heads 362, 382 are located inside the closed cavity.

Figure 30:
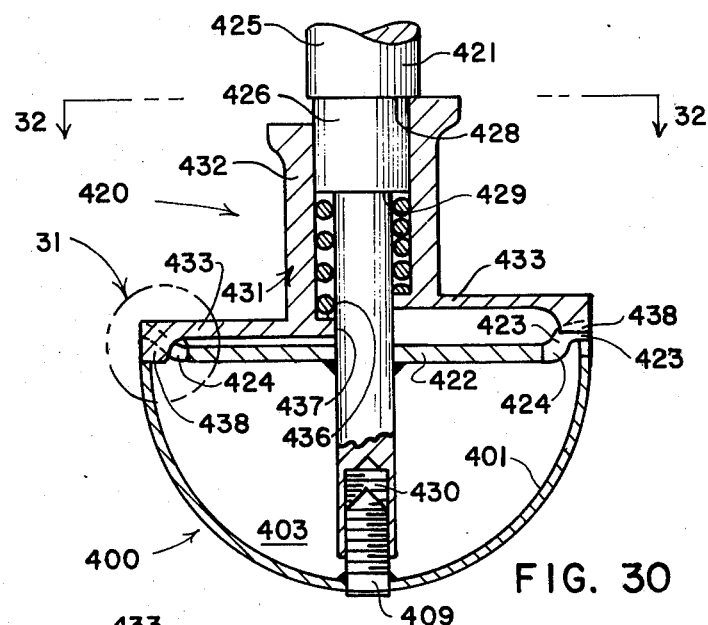
FIG. 30 is a side elevational view of an alternate tool body and tool support, the right and left side portions of the view showing certain components of the support in different positions, portions of the view being broken away and shown in cross-section to illustrate detail.
Figure 31:
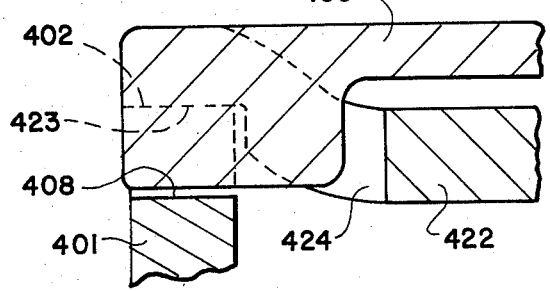
FIG. 31 is an enlarged showing of a portion of the structure of FIG. 30.
Figure 32:
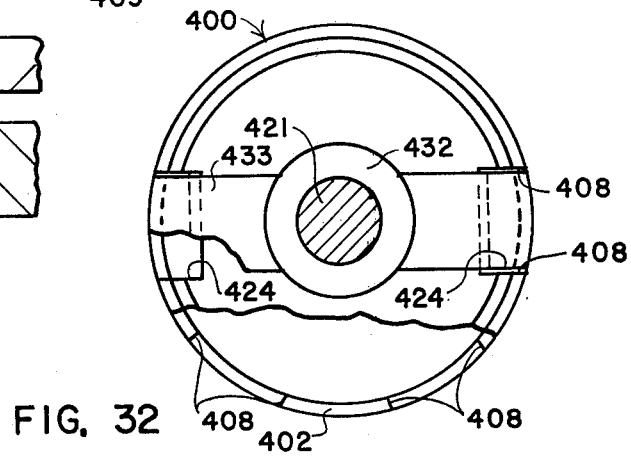
FIG. 32 is a sectional view as seen from a plane indicated by a line 32—32 in FIG. 31.

Referring to FIGS. 30-32, alternate embodiments of a milling tool and a milling tool support are indicated generally by the numerals 400, 420.

The milling tool 400 is constructed the same as the tool 100 in its provision of a hollow body 401 which has a rim 402 and which defines a cavity 403. Although some features of the tool 400 do not show in FIG. 30, it will be understood that the tool 400 has milling blades formed on cup-like projections with cooperating holes to channel cut-off tissues into the cavity 403, as is described in conjunction with the tool 100.

In order to facilitate the forming of a driving connection between the tool 400 and the support structure 420, a plurality of notches 408 are formed at circumferentially spaced locations around the tool rim 402. A threaded fastener 409 is welded to the tool body 401 and projects upwardly inside the cavity 403.

The tool support 420 includes a shaft 421. An enlarged diameter annular mounting head 422 is positioned around and is welded to the shaft 421. The head 422 extends in a planar fashion radially outwardly from the shaft 421 toward the rim 402 of the tool 400. In the vicinity of the rim 402, the head 422 has an upwardly and outwardly curved lip 423 which overlies the rim 402. A feature of the mounting head 422 is that it forms a cover which closes the open end of the tool cavity 403 to retain tissue materials within the cavity 403.

Two notches 424 are formed in opposite sides of the lip 423. The notches 424 are alignable with a selected pair of the tool notches 408.

The shaft 421 has a relatively large diameter upper end portion 425, a reduced diameter intermediate portion 426, a further reduced diameter lower end portion 427. Radially extending shoulders 428, 429 connect the portions 425, 426 and 426, 427. A threaded axially extending hole 430 is formed in the lower portion 427 to receive the threaded tool fastener 409.

A locking structure 431 is positioned on the shaft 421 above the head 422 and below the shoulder 428. The locking structure includes an upstanding sleeve 432 and an integrally formed radially extending member 433. The sleeve 432 has a stepped bore with a large diameter upper end 435 connected by a radially extending shoulder 436 with a smaller diameter lower end 437. The upper end 435 slip fits on the shaft portion 426. The lower end 437 slip fits on the shaft portion 427.

A pair of depending projections 438 are provided on the outer end regions of the radially extending member 433. The projections 438 extend into aligned pairs of the notches 408, 424 to establish a driving connection between the head 422 and the tool 400 when the locking structure is in its downward position as shown in the left side of FIG. 30.

The locking structure 431 is movable upwardly along the shaft 421 to remove the projections 438 from the tool notches 408. Upward movement of the locking structure 431 is limited by engagement of the top of the sleeve 432 with the shaft shoulder 428, as shown in the right side of FIG. 30.

A compression coil spring 439 is positioned in the upper bore region 435 to bias the locking structure 431 to its downward position. One end of the spring 439 engages the shaft shoulder 429. The other end of the spring 439 engages the sleeve should 436.

The tool 400 is mounted on the support 420 by threading the fastener 409 into the shaft hole 430 while the locking structure 431 is in its upward position. Once the rim 402 of the tool 400 has been brought into engagement with the lip 423, a pair of the tool notches 408 are aligned with the member notches 424, and the locking structure 431 is lowered to extend the projections 438 into the aligned notches 408, 424. Removal of the tool 400 from the mounting head 420 is effected by reversing these steps. FIGS. 33, 34 and 35, 36, and 37, 38 illustrate three further alternate embodiments of milling tools 500, 600, 700 and tool supports 520, 620, 720.

The milling tools 500, 600, 700 are constructed the same as the tool 100 in their provisions of hollow bodies 501, 601, 701 which have rims 502, 602, 702 and which define central tissue-receiving cavities 503, 603, 703. Although some features of the tools 500, 600, 700 do not show in FIGS. 33–38, it will be understood that each of the tools 500, 600, 700 has milling blades formed on cup-like projections with cooperating holes to channel cut-off tissues into the cavities 503, 603, 703, as is described in conjunction with the tool 100.

The tools 500, 600 have rims 502, 602 which extend radially inwardly for connection to their tool supports 520, 620. The rim 502 of the tool 500 terminates to define a central opening 508. The rim 602 of the tool 600 extends axially upwardly to define a central opening 608.

Referring to FIGS. 33 and 34, the tool support 520 includes a shaft 521 and an enlarged diameter, integrally formed tool mounting head 522. A reduced diameter projection 523 is provided on the head 522. A pair of radially projecting pins 524 are rigidly carried by the projection 523.

A pair of slots 509 are formed through the tool rim 502 adjacent the central opening 508 to permit the head projection 523 and the pins 524 to be introduced into the cavity 503. A pair of depending formations 510 are provided in the tool rim 502 to mate with the pins 524 and establish a rigid releasable connection between the tool 500 and the support 520. Upwardly extending depressions 511 are provided in the formations 510 to seat the pins 524. Depending stops 512 are formed adjacent the depressions 511 to enable the transmission of driving torque from the head 522 to the tool 500 through the pins 524.

The tool 500 is mounted on the support 520 by moving the tool 500 axially of the support 520 to extend the projecting portion 523 through the central opening 508 and to extend the pins 524 through the slots 509. The tool 500 is then rotated relative to the support to move the pins 524 along the undersides of the formations 510 and into seating engagement with the depressions 511. Removal of the tool 500 from the support 520 is effected by reversing these steps.

Referring to FIGS. 35 and 36, the tool support 620 includes a shaft 621 and an enlarged diameter integrally formed mounting head 622. The head 22 is cylindrical and has a circumferentially extending groove 623. A radially compressible resilient ring 624 is positioned in the groove 623 and has an outer diameter which is normally greater than the inner diameter of the central tool opening 608.

A pair of slots 625 are formed in opposite sides of the tool rim 602. A pair of radially extending projections 626 are formed on the head 622. The projections 626 are configured to mate with the slots 625 to establish a driving connection between the tool 600 and the support 620.

The tool 600 is mounted on the support 620 by moving the tool 600 axially relative to the support to extend the head 622 and the ring 624 through the central opening 608 for positioning as shown in FIG. 35. In the mounted position shown in FIG. 35, the resilient ring 624 has expanded radially inside the cavity 603 to releasably hold the tool 600 on the support 620, and the projections 626 are received in the notches 625 and abut the upper surface of the rim 602 to complete the formation of a driving connection between the tool 600 and the support 620. Removal of the tool 600 from the support 620 is effected by simply pulling the tool 600 axially downwardly to release its connection with the support head 622.

A feature of the support heads 522, 622 is that they close the central tool openings 508, 608 to inhibit the discharge of tissue materials from the cavities 503, 603. An additional feature of the support heads 522, 622 is that milling tools of different sizes but each having a common central opening size can easily be interchanged and mounted on the supports 520, 620.

Figure 37:
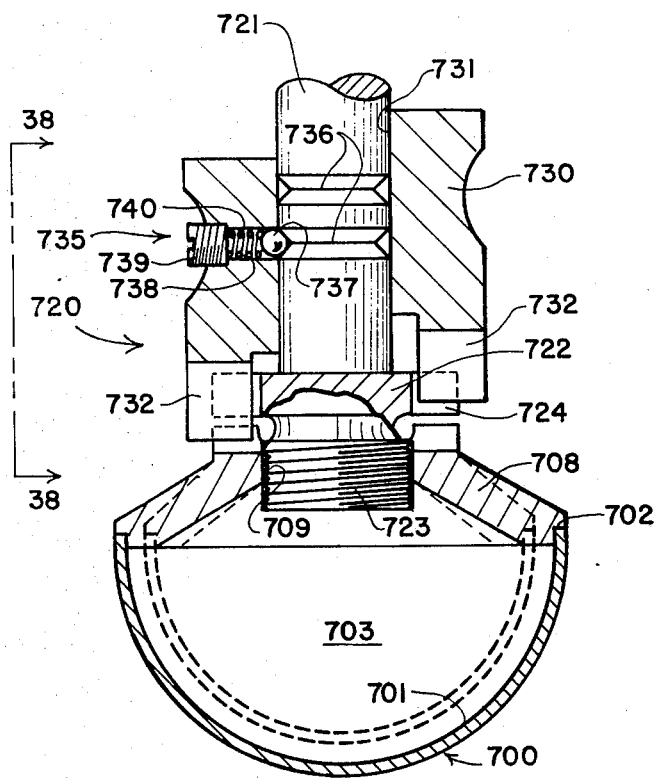
FIG. 37 is a side elevational view of an alternate tool body and tool support, the right and left side portions of this view showing certain of the tool support components in different positions, portions of the view being broken away and shown in cross-section to illustrate detail.
Figure 38:
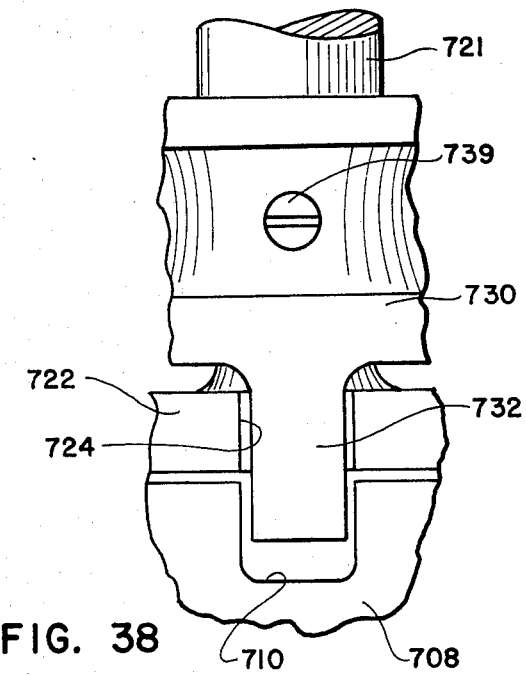
FIG. 38 is an enlarged side elevational view of a portion of the structure of FIG. 37 as seen from a plane indicated by a line 38—38 in FIG. 37.

Referring to FIGS. 37 and 38, the milling tool 700 has a conical-shaped annular flange member 708 welded to the rim 702 of the tool body 701. Internal threads 709 are provided in the flange member 708. A pair of notches 710 are formed in the upper end of the flange member 708.

The tool support 720 includes a shaft 721 having an enlarged diameter mounting head 722 formed integrally near its lower end. External threads 723 are formed on the head 722. The external head threads 723 engage the flange member threads 709 to interconnect the tool 700 and the head 722. A pair of notches 724 are formed in opposite sides of the head 722. The head notches 722 are alignable with the flange member notches 710 as is best seen in FIG. 38.

A locking sleeve 730 is movably carried on the shaft 721. The sleeve 730 has an axial hole 731 which is slip fitted on the shaft 721. A pair of depending projections 732 are carried on the sleeve 730 for extension into the aligned notches 724, 710. When the sleeve 730 is in its downward position, as shown in the left side of FIG. 37, the projections 732 extend into the aligned notches 724, 710 and establish a driving connection between the head 722 and the tool 700. When the sleeve 730 is moved upwardly to the position shown in the right side of FIG. 37, the projections 732 disengage the flange member notches 710.

A ball detent assembly 735 is carried in the sleeve 730 to selectively engage a pair of axially spaced grooves 736 formed in the shaft 721. The detent assembly 735 includes a hardened ball 737 positioned at the inward end of a radially extending hole 738. A setscrew 739 is threaded into the outer end of the hole 739. A compression coil spring 740 is interposed between the setscrew 739 and the ball 737 to bias the ball 737 radially inwardly of the hole 738. When the ball 737 engages one of the grooves 736, it operates to releasably retain the sleeve 730 in one of the two positions shown in FIG. 37.

The tool 700 is mounted on the support 720 by first moving the sleeve 730 to its upward position as shown in the right side of FIG. 37. The flanged member 708 is then threaded onto the head 722 to a position where the slots 710, 724 align. The sleeve 730 is then moved downwardly to the position shown in the left side of FIG. 37 where the projections 732 engage the slots 710. Removal of the tool 700 from the support 720 is effected by reversing these steps.

A feature of the tool support 720 is that the head 722 closes the threaded opening in the flanged member 708. An additional feature is that milling tools having a smaller outer diameter but having the same size threaded flange opening can be readily attached to the head 722, as shown in phantom in FIG. 37.

Referring to FIGS. 39–42 on alternate tool support embodiment which is usable with a slightly modified form of the tool 100 is indicated generally by the numeral 820. The only modification which is required in the tool 100 to adapt it for use with the support 820 is the addition of two notches 808 in opposite sides of the tool rim 102.

The tool support 820 is quite similar to the tool support 120 in its inclusion of a shaft 821, an integrally formed mounting head 822, integrally formed hook formations 824, and a circumferentially extending recess 823 configured to receive the rim 102 of the tool body 101. A feature of the mounting head 822 is that it forms a cover which closes the open end of the tool cavity 103 to retain tissue materials within the cavity 103.

A pair of notches 825 are formed in opposite sides of the head 822. The notches 825 open through the recess 824. A slide 826 is slidably supported on the underside of the head 822. The slide 826 has enlarged end regions 827 which are normally received in the notches 808, 825. The slide 826 has an intermediate region 828 of reduced cross-section which extends between the enlarged end regions 827.

A plate 829 underlies the intermediate region 828 and is secured to the head 822 by threaded fasteners 830. The fasteners 830 position the plate 829 to permit longitudinal sliding movement of the slide 826. The slide 826 is movable to the position shown in phantom in FIG. 39 where the end regions 827 no longer engage the tool notches 808.

Figure 39:
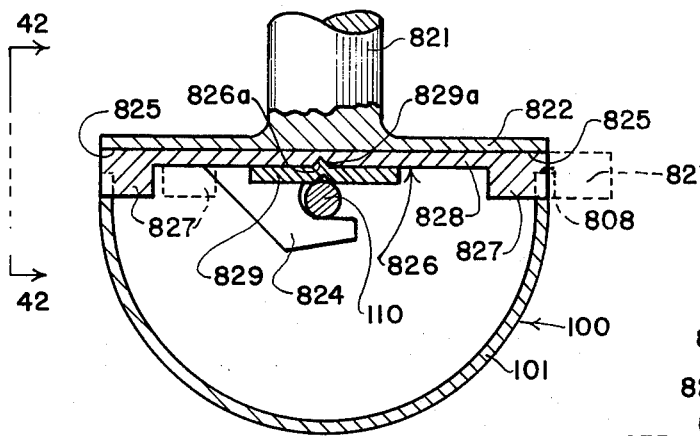
FIG. 39 is a side elevational view of the tool body of FIG. 1 carried on an alternate tool support embodiment, portions of the view being broken away and shown in cross-section to illustrate detail.

The tool 100 as modified to include the notches 808 is mounted on the support 820 after the slide 826 has been moved to the position shown in phantom in FIG. 39 in exactly the same fashion as the tool 100 is mounted on the support 120. After the tool 100 is mounted on the support 820, the slide 826 is moved longitudinally to the position shown in solid lines in FIG. 39 where the end regions 828 engage the tool notches 808 to prevent relative rotation of the tool 100 and the head 822. Removing the tool 100 from the support 820 is effected by reversing these steps.

Figure 40:
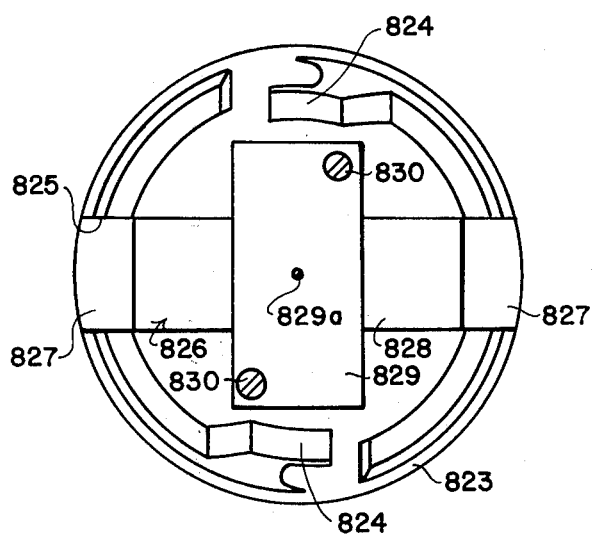
FIG. 40 is a bottom plane view of the tool support of FIG. 39 with the tool body removed.
Figure 42:
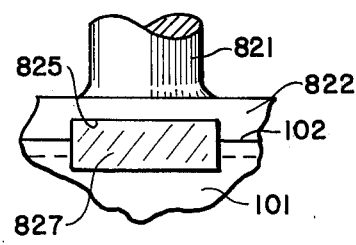
FIG. 42 is a side elevational view of a portion of the tool body and tool support of FIG. 39, as seen from a plane indicated by a line 42—42 in FIG. 39.

Referring to FIGS. 39, 40 a raised dimple 829a is formed centrally in the plate 829. A depression 826a formed in the underside of the slide 826. The dimple 829a engages the depression 826a when the slide 826 is positioned as shown in solid lines in FIG. 39 to hold the slide 826 in this position. When the slide 826 is moved longitudinally, the plate 829 deforms to permit the dimple 829a to pass along the underside of the slide 826.

Figure 41:
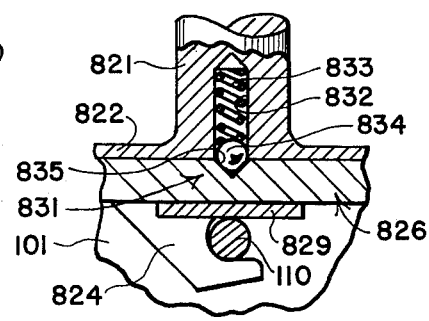
FIG. 41 is a side elevational view of a slightly modified form of the support of FIG. 39, portions of the view being broken away and shown in cross-section to illustrate detail.

Referring to FIG. 41, an alternate means of retaining the slide 826 in a centered position employs a ball detent assembly 831. An axially extending hole 832 is formed in the underside of the head 822. A compression coil spring 833 and a hardened ball 834 are positioned in the hole 832 such that the spring 833 biases the ball 834 downwardly into engagement with the upper surface of the slide 826. A depression 835 is formed in the upper surface of the slide 826 to receive the ball 834 when the slide 826 is positioned as shown in solid lines in FIG. 39.

Figure 43:
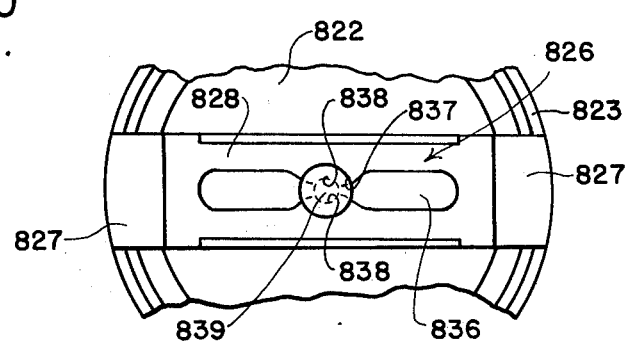
FIG. 43 is a bottom plane view of slightly modified form of the tool support of FIG. 39 with the tool body removed.
Figure 47:
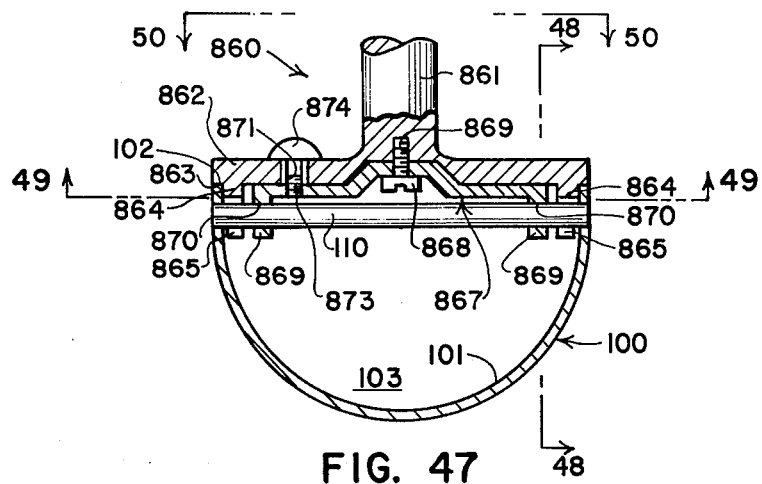
FIG. 47 is a side elevational view of the tool body of FIG. 1 as carried on an alternate tool support, portions of the view being broken away and shown in cross-section to illustrate detail.
Figure 48:
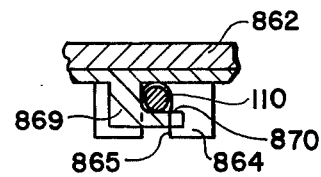
FIG. 48 is a sectional view as seen from a plane indicated by a line 48—48 in FIG. 47.
Figure 49:
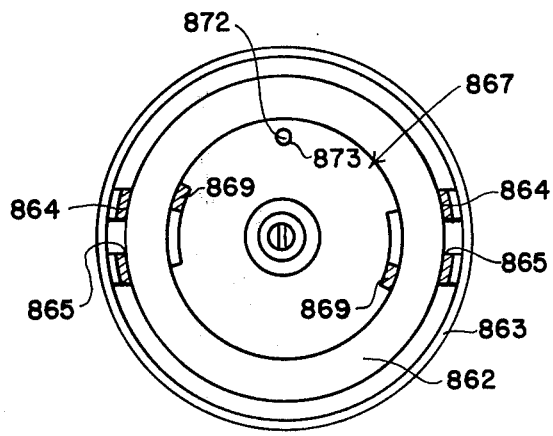
FIG. 49 is a cross-sectional view as seen from a plane indicated by a line 49—49 in FIG. 47.
Figure 50:
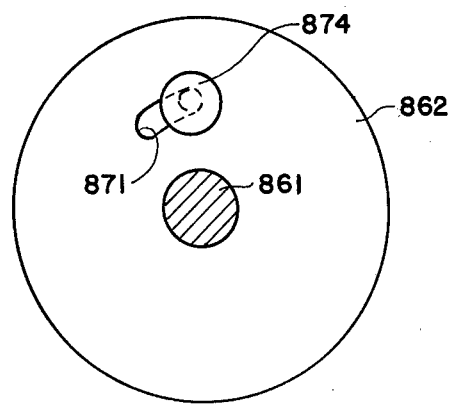
FIG. 50 is a cross-sectional view as seen from a plane indicated by line 50—50 in FIG. 47.
Figure 51:
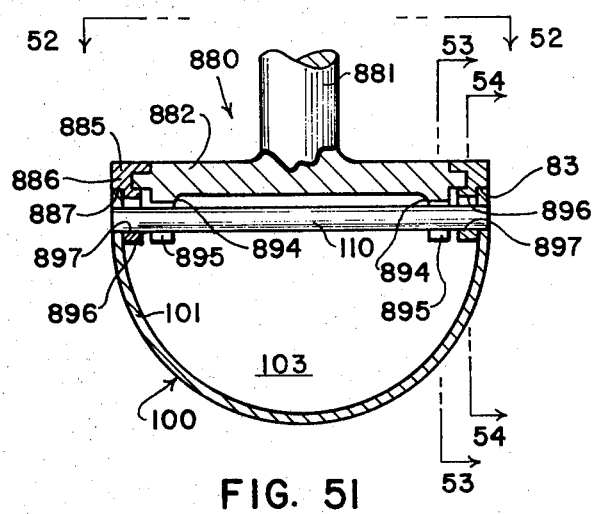
FIG. 51 is a side elevational view of the tool body of FIG. 1 as carried on an alternate support, portions of the view being broken away and shown in cross-section to illustrate detail.
Figure 53:
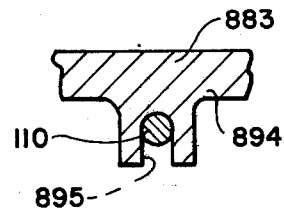
FIGS. 52, 53, 54 are cross-sectional views as seen from planes indicated by lines 52—52, 53—53, 54—54 in FIG. 51.
Figure 52:
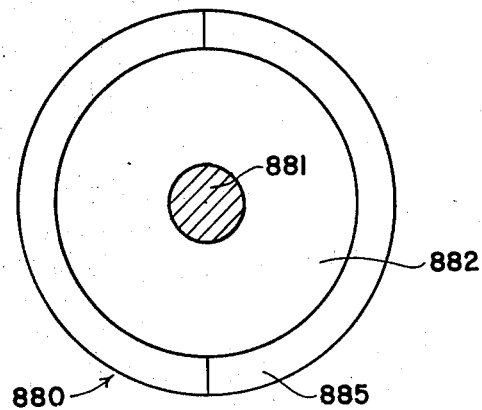
Figure 54:
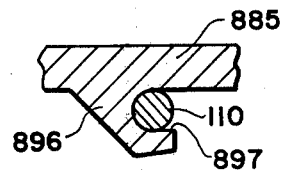

Still another alternate arrangement for releasably retaining the slide 826 in a centered position is illustrated in FIG. 43. A longitudinally extending slot 836 is formed in the intermediate region 828 of the slide 826. The slot 836 narrows in a central region 837 and is provided with two depressions 838 which face toward each other. A fastener or pin-like member 839 is carried by the head 822 and extends into the slot 836. When the slide 826 is centered along its path of travel, the pin-like fastener portion 839 is received in the depressions 838. The resilient nature of the material from which the slide 826 is formed permits sufficient deformation of the slide 826 for the pin 839 to pass through narrow portions 837 of the slot 836 which are located on either side of the depressions 838.

Referring to FIGS. 44–46, an alternate tool support embodiment which can be used with the milling tool 100 is indicated generally by the numeral 840. The support 840 includes a shaft 841 and an enlarged diameter mounting head 842 formed integrally with the shaft 841. The head 842 has another diameter which is substantially the same as the outer diameter of the tool body 101. A circumferentially extending recess 843 is formed in the head 842 and is configured to receive the rim 102 of the tool body 101. A feature of the mounting head 842 is that it forms a cover cavity 103 to retain tissue materials within the cavity 103.

A pair of projections 844 are formed integrally with the head 842 and depend into the tool cavity 103. A pair of notches 845 are formed in the projections 844 to receive the tool rod 110. The notches 845 function in a similar fashion to the notches 145 (FIGS. 4, 6) formed in the tool support head 142 to transmit rotary torque from the support 840 to the tool 100.

A pair of openings 847 are formed through opposite sides of the head 842. A slide structure 846 extends through the openings 847. The slide structure 846 has opposite end regions 848 which overlie peripheral portions of the head 842, and a central portion 849 which underlies the central region of the head 842. A hook-shaped depending projection 850 is formed integrally on the slide 846. A notch 851 is formed in the projection 850 to receive a central region of the tool rod 110.

A pair of finger engaging depressions 852 are formed in the slide end regions 848. The slide 846 is movable leftwardly, as viewed in FIGS. 44, 45, to disengage the hook-shaped projections 850 from the tool rod 110.

A ball detent assembly 853 is provided on the support 840 to hold the slide 846 in the centered position shown in FIG. 44. An axially extending hole 854 is formed in the underside of the head 842. A compression coil spring 855 and a hardened ball 856 are positioned in the hole 854 such that the spring 855 biases the ball 856 downwardly into engagement with the upper surface of the slide 846. A depression 857 is formed in the upper surface of the slide 846 to receive the ball 856 when the slide 846 is centered as shown in FIG. 44.

The tool 100 is mounted on the support 840 by moving the slide 846 leftwardly, as viewed in FIG. 44, to a position where the projection 850 will not interfere with positioning the tool rod 110 in the slots 845. The tool 100 is then positioned on the support 840 with its rod 110 received in the slots 845, and the slide 846 is moved rightwardly to engage the rod 110 in the slot 851. Removing the tool 100 from the support 840 is effected by reversing these steps.

Referring to FIGS. 47–50, an alternate tool support embodiment which can be used with the milling tool 100 is indicated generally by the numeral 860. The support 860 includes a shaft 861 and an enlarged diameter mounting head 862 formed integrally with the shaft 861. The head 862 has an outer diameter which is substantially the same as the outer diameter of the tool body 101. A circumferentially extending recess 863 is formed in the head 862 and is configured to received the rim 102 of the tool body 101. A feature of the mounting head 862 is that it forms a cover which closes the open end of the tool cavity 103 to retain tissue materials within the cavity 103.

A pair of projections 864 are formed integrally with the head 862 and depend into the tool cavity 103. A pair of notches 865 are formed in the projections 864 to receive the tool rod 110. The projections 864 function similarly to the projections 844 (FIGS. 44, 46) formed in the tool support head 842 to transmit rotary torque from the support 860 to the tool 100.

A rotary slide or disc-like locking member rotatably supported on the underside of the head 862 to hold the tool 100 in place on the head 862. A threaded fastener 868 extends through a central hole in the locking member 867 and is threaded into an axially extending hole 869 in the head 862. The fastener 868 has a head which underlies portions of the locking member 867 and mounts the locking member for rotation about the axis of the fastener 868.

A pair of hook-shaped projections 869 depend from peripheral portions of the disc-like locking member 867. Slots 870 are formed in the projections 869 to receive the tool rod 110.

An arcuate slot 871 is formed through the mounting head 862. A threaded hole 872 is formed in the locking member 867 at a location aligned with the slot 871. A threaded fastener 873 having a knob-like head 874 extends through the slot 871 and is threaded into the hole 872. The knob-like head 874 enables an operator to rotate the locking member 867 from a position where the slots 870 receive the tool rod 110 to a position where the tool rod 110 is removed from the slots 870.

The tool 100 is mounted on the support 860 by rotating the locking disc 867 to a position where the projections 869 do not interfere with inserting the tool rod 110 into the slots 865. The tool 100 is then positioned on the support 860 with its rod 110 received in the slots 865. The tool 100 is locked in place by rotating the locking disc 867 to the position shown in FIGS. 47–49 where the rod 110 is received in the slots 870. Removing the tool 100 from the support 860 is effected by reversing these steps.

Referring to FIGS. 51–54, still another alternate tool support embodiment which can be used with the milling tool 100 is indicated generally by the numeral 880. The support 880 includes a shaft 881 and an enlarged diameter mounting head 882 formed integrally with the shaft 881. A ring 885 extends circumferentially around the head 882. A radially extending flange 886 is formed on the periphery of the head 882 and extends into a groove 887 in the ring 885 to mount the ring 885 for rotation relative to the head 882.

The ring 885 has an outer diameter which is substantially the same as the outer diameter of the tool body 101. A circumferentially extending recess 883 is formed in the ring 885 and is configured to receive the rim 102 of the tool body 101. A feature of the mounting head 882 and the ring 885 is that these components cooperate to define a cover which closes the open end of the tool cavity 103 to retain tissue materials within the cavity 103.

A pair of projections 894 are formed integrally with the head 882 and depend into the tool cavity 103. A pair of downwardly opening notches 895 are formed in the projections 894 to receive the tool rod 110. The projections 894 are operative to transmit rotary torque from the support 880 to the tool 100.

A pair of hook-shaped projections 896 depend from opposite sides of the ring 885. Slots 897 formed in the projections 896 to receive the tool rod 110. The slots 897 face in opposite directions to enable their concurrent disengagement from the tool rod 110 as by rotating the ring 885 relative to the head 882.

The tool 100 is mounted on the support 880 by rotating the ring 885 to a position where the ring-carried projections 896 do not interfere with inserting the tool rod 110 into the slots 895. The tool 100 is then positioned on the support 880 with its rod 110 received in the slots 895. The tool 100 is locked in place by rotating the ring 885 to the position shown in FIGS. 51, 54 where the rod 110 is received in the slots 897. Removing the tool 100 from the support 880 is effected by reversing these steps.

FIGS. 55–59 and 60–62 illustrate two further alternate embodiments of milling tools 900, 1000 and tool supports 920, 1020.

The milling tools 900, 1000 are constructed the same as the tool 100 in their provisions of hollow bodies 901, 1001 which have rims 902, 1002 and which define central tissue-receiving cavities 903, 1003. Although some features of the tools 900, 1000 do not show in FIGS. 55–62, it will be understood that each of the tools 900, 1000 has milling blades formed on cup-like projections with cooperating holes to channel cut-off tissues into the cavities 903, 1003 as is described in conjunction with the tool 100.

Figure 55:
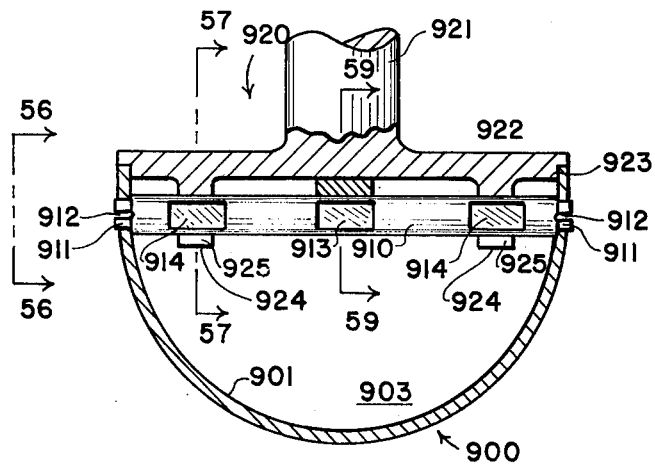
FIG. 55 is a side elevational view of alternate tool body and tool support embodiments, portions of the view being broken away and shown in cross-section to illustrate detail.
Figure 56:
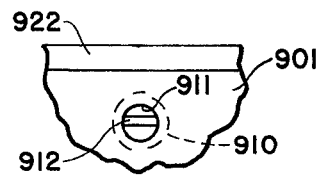
FIG. 56 is a side elevational view of a portion of the tool body and tool support shown in FIG. 55.
Figure 59:
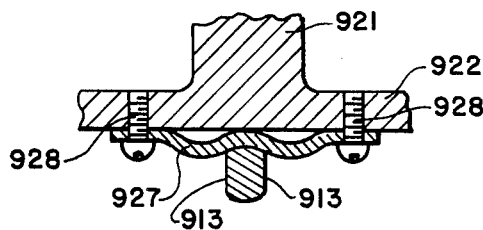
FIG. 59 is a sectional view as seen from a plane indicated by a line 59—59 in FIG. 55.

The tool 900 has aligned holes 911 formed through opposite sides at a short distance below the rim 902. A tool rod 910 extends through the cavity 903 and has its reduced diameter ends journaled in the holes 911. Tool receiving slots 912 are formed in opposite ends of the rod 910. As is best seen in FIG. 59, flats 913 are formed on opposite sides of the rod 910 at a central location along the length of the rod 910. As is best seen in FIGS. 55 and 57, two pairs of flats 914 are formed on opposite sides of the rod 910 at positions spaced a short distance inwardly from the ends of the rod 910.

The tool support 920 includes a shaft 921 and an enlarged diameter integrally formed tool mounting head 922. The head 922 has an outer diameter which is substantially the same as the outer diameter of the tool body 901. A circumferentially extending recess 923 is formed in the head 922 and is configured to receive the rim 902 of the tool body 901. A feature of the mounting head 922 is that it forms a cover which closes the open end of the tool cavity 903 to retain tissue materials within the cavity 103.

A pair of projections 924 are formed integrally with the head 922 and depend into the tool cavity 903. A pair of downwardly opening slots 925 are formed in the projections 924. As is best seen in FIG. 57, the slots 925 have parallel walls which extend upwardly from the bottom surfaces of the projections 924. The parallel walls are joined by an arcuately curved wall which has an inner diameter that will loosely receive the tool rod 910. The parallel walls of the slots 925 are spaced to permit portions of the rod 910 intermediate the flats 914 to pass therebetween.

Figure 57:
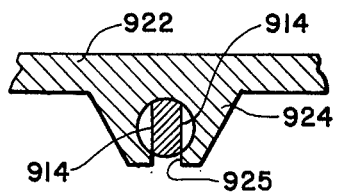
FIG. 57 is a sectional view as seen from a plane indicated by a line 57—57 in FIG. 55.
Figure 58:
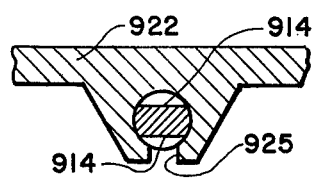
FIG. 58 is a sectional view as seen from the plane indicated by the line 57—57 in FIG. 55, with portions of the tool body repositioned to lock the tool body onto the support.

The tool rod 910 is rotatable from the unlatched position shown in FIG. 57 where the flats 914 align with the parallel walls of the slots 925, to a latched position shown in FIG. 58 where the flats 914 extend orthogonally of the parallel walls of the slots 925. Rotation of the rod 910 is effected by inserting a flattened tool such as a screwdriver in one of the rod slots 912 to turn the rod 910.

Referring to FIG. 59, a spring plate 927 is provided on the underside of the head 922 to engage central portions of the rod 910. Threaded fasteners 928 extend through the plate 927 and are threaded into the head 922 to hold the spring plate 927 in place on the head 922. When the tool rod 910 is rotated to the latched position shown in FIG. 58, the spring plate 927 engages one of the rod flats 913 and helps to retain the rod 910 in its latched position.

The tool 900 is mounted on the support 920 by first rotating the rod 910 to its unlatched position. The tool 900 is then moved axially toward the support 920 and the rod flats 914 are inserted into the slots 925. Once the tool 900 is positioned on the support 920 as shown in FIG. 55, the rod 910 is rotated to its latched position to retain the tool 900 on the support 920. Removal of the tool 900 from the support 920 is effected by reversing these steps.

Figure 60:
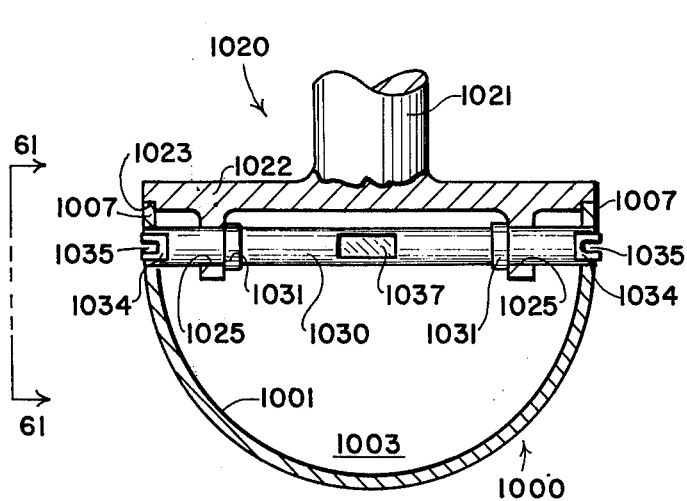
FIG. 60 is a side elevational view of an alternate tool body and tool support embodiment with portions of the view being broken away and shown in cross-section to illustrate detail.
Figure 61:
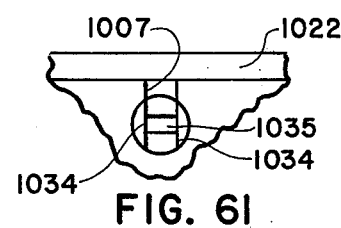
FIG. 61 is a side elevational view of a portion of the tool body and tool support of FIG. 60 as seen from a plane indicated by a line 61—61 in FIG. 60; and, FIG. 62 is a side elevational view as seen from the plane indicated by the line 61 with portions of the tool support repositioned to retain the tool body on the tool support.
Figure 62:
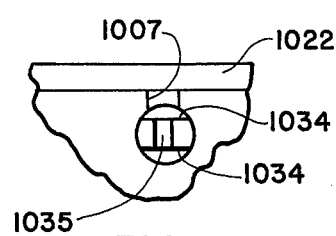

Referring to FIGS. 60–62, the tool 1000 has a pair of slots 1007 formed in its opposite sides and opening through the tool rim 1002. The slots 1007 have spaced parallel walls which extend downwardly away from the rim 1002 and which are interconnected by an arcuately curved wall.

The tool support 1020 includes a shaft 1021 and an enlarged diameter integrally formed tool mounting head 1022. The head 1022 has an outer diameter which is substantially the same as the outer diameter of the tool body 1001. A circumferentially extending recess 1023 is formed in the head 1022 and is configured to receive the rim 1002 of the tool body 1001. A feature of the mounting head 1022 is that it forms a cover which closes the open end of the tool cavity 1003 to retain tissue materials within the cavity 1003.

A pair of projections 1024 are formed integrally with the head 1022 and depend into the tool cavity 1003. Aligned holes 1025 are formed through the projections 1024. A tool mounting rod 1030 extends through and is journaled in the holes 1025. A pair of collars 1031 are carried on the rod 1030 and engage the inner walls of the projections 1024 to restrain the rod 1030 from moving axially.

Pairs of flats 1034 are formed on opposite end regions of the rod 1030. The flats of each pair 1034 are parallel and are spaced such that they will slip fit between the parallel walls of the slots 1007. Tool receiving notches 1035 are formed in the ends of the rod 1030 and extend orthogonally of the flats 1034.

A pair of flats 1037 are formed on central portions of the rod 1030, in the manner of the described flats 913. A detent assembly of the type shown in FIG. 59 is provided on the tool head 1022 to retain the rod 1030 in the latched position shown in FIG. 62 where the flats 1034 extend orthogonally relative to the parallel walls of the slots 1007.

The rod 1030 is rotatable to an unlatched position shown in FIG. 61 where the flats 1034 align with the parallel walls of the slots 1007. Rotation of the rod 1030 is effected by inserting a flattened tool such as a screwdriver into one of the notches 1035.

The tool 1000 is mounted on the support 1020 by first rotating the rod 1030 to its unlatched position. The tool 1000 is then moved axially toward the support 1020 and the rod flats 1034 are inserted into the slots 1007. Once the tool 1000 is positioned on the support 1020 as shown in FIG. 60, the rod 1030 is rotated to its latched position to retain the tool 1000 on the support 1020. Removal of the tool 1000 from the support 1020 is effected by reversing these steps.

From the foregoing description, it will be apparent that the present invention provides novel and improved milling apparatus embodiments which have in common a substantially hemispherically milling tool which is removably carried on a support that closes an open end of a cavity defined within the tool. Some of the embodiments include movable latching members which help retain their tools on their supports. In all cases, a rapid latching and unlatching of the tools from their supports can easily be effected either by hand or through the use of a simple tool.

Although the invention has been described in its preferred form with a certain degree of particularly, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A milling tool for use in milling tissues from a joint socket in the prosthetic replacement of a joint, comprising:
   a. a hollow body having a substantially hemispherical outer surface and defining an internal cavity, the body having a rim which extends around an open end of the cavity;
   b. a plurality of blades carried in spaced relationship on the outer surface of the body;
   c. opening means including a plurality of openings formed through the outer surface and communicating with the cavity, at least a separate one of the openings being associated with each of the blades and being operable to channel tissue materials which have been cut off by the blades into the cavity; and
   d. tool support means drivingly connected to the body for positioning and rotating the body, the support means including a cover which releasably closes the open end of the cavity.

2. The milling tool of claim 1 wherein mating formations are carried on the body and on the support means for releasably drivingly connecting the body and the support means.

3. The milling tool of claim 2 additionally including biasing means carried by a selected one of the support means and the body for retaining mating engagement between the mating formations.

4. The milling tool of claim 2 additionally including a locking member movably carried by a selected one of the support means and the body for releasably retaining mating engagement between the mating formations.

5. The milling tool for claim 4 additionally including biasing means carried by a selected one of the support means and the body for releasably retaining the movable locking member in a locked position.

6. The milling tool of claim 1 wherein the cover includes a circumferentially extending recess configured to receive the body rim.

7. The milling tool of claim 1 wherein:
   a. the support means includes a rotatable drive member;
   b. at least one portion of the cover is rigidly secured to the drive member; and c. mating formations are carried on the body and on the one cover portion to drivingly interconnect the drive member and the body.

8. The milling tool of claim 7 additionally including a locking member movably carried by a selected one of the support means and the body for releasably retaining mating engagement between the mating formations.

9. The milling tool of claim 1 wherein the support means additionally includes a rotatable drive shaft, and the cover is releasably connected to the drive shaft.

10. The milling tool of claim 1 wherein the support means additionally includes a rotatable drive shaft, and at least a portion of the cover is rigidly and permanently connected to the drive shaft.

11. The milling tool of claim 1 wherein the support means includes a rotatable drive shaft and the cover is formed integrally with the drive shaft.

12. The milling tool of claim 1 wherein:
a. a rod extends through the cavity and has its opposite end regions connected to the body; and
b. at least one rod engaging formation is carried on the support means for releasably engaging the rod to establish a connection between the support means and the tool body.

13. The milling tool of claim 12 wherein:
a. the support means includes a rotatable drive member and at least one additional member which is movable relative to the drive member; and
b. at least one separate rod engaging formation is provided on each of the drive members and the additional member.

14. The milling tool of claim 13 wherein the additional member forms at least a portion of said cover.

15. The milling tool of claim 12 wherein the rod engaging formation is carried on said cover.

16. The milling tool of claim 12 wherein said at least one rod engaging formation includes a pair of hook-shaped projections which depend from the support means into the cavity to engage the rod.

17. The milling tool of claim 12 wherein said at least one rod engaging formation includes formations on the support means defining a pair of spaced slots which are engagable with the rod.

18. The milling tool of claim 1 wherein a driving connection is established between the tool support means and the tool body by means of at least one latch formation carried on a selected one of the support means and the body, and by at least one latch member which is movably carried by the other of the support means and the body and which is releasably engagable with the latch formation.

19. The milling tool of claim 18 wherein said at least one latch formation is carried on the body, and said at least one latch member is carried on the support means.

20. The milling tool of claim 18 wherein said at least one latch formation is carried on the support means, and said at least one latch member is carried on the body.

21. The milling tool of claim 18 wherein said at least one latch member is mounted for movement about an axis between latched and unlatched positions.

22. The milling tool of claim 21 wherein the latch member includes a lever pivotally mounted on the support means for movement between latched and unlatched positions where the lever engages an apertured latch formation on the tool body.

23. The milling tool of claim 22 wherein the lever is carried in a slot formed in the support means.

24. The milling tool of claim 1 wherein:
a. the support means includes a member which is rotatable about an axis;
b. the cover is threadedly connected to the rotatable member for rotation about said axis;
c. at least one hook-like formation is carried on the rotatable member and depends into the cavity;
d. at least one hook-engaging formation is carried on the body for releasably engaging the hook-like formation; and
e. the cover is operable when rotated about said axis to selectively releasably clamp said formations into locking engagement.

25. The milling tool of claim 1 wherein:
a. at least one rod-like radially extending formation is carried on the support means;
b. at least one apertured formation is provided in the tool body and releasably receives the rod-like formation;
c. said formations being operable to establish a releasable driving connection between the support means and the tool body.

26. The milling tool of claim 25 wherein said rod-like formation includes a pair of pins carried on the support means, and said apertured formation includes a pair of slots formed in the tool body, each of the slots receiving portions of a separate one of the pins.

27. The milling tool of claim 26 wherein said slots each have at least one inclined wall which engages its associated pin and assists in clamping the tool body into engagement with the support means.

28. The milling tool of claim 26 wherein:
a. the support means includes a rotatable member which carries said pins;
b. the cover is threaded onto the drive member; and
c. the cover is movable as by threading it along the drive member to a position where the cover helps retain the pins in the slots.

29. The milling tool of claim 25 wherein the rod-like formation is supported on resilient means and the resilient means is supported by the support means.

30. The milling tool of claim 25 wherein the rod-like formation is biased toward a position of engagement with the apertured formation.

31. The milling tool of claim 26 wherein the support means includes at least one resilient member having spaced first and second portions, said first portions being secured to the cover and said second portions carrying said pins.

32. The milling tool of claim 26 wherein said slots are provided with depressions which seat said pins and assist in retaining said pins in said slots.

33. The milling tool of claim 1 wherein:
a. at least one apertured formation is provided in the tool body;
b. the support means includes at least one resilient member which is movable to selectively project portions of the resilient member into the apertured formation to establish a connection between the tool body and the support means.

34. The milling tool of claim 33 wherein:
a. the support means is rotatable about an axis;
b. the projecting portions of the resilient member extend generally radially of said axis; and
c. other portions of the resilient member are movable axially of said axis to effect radial movement of the projecting portions into and out of engagement with the apertured formation on the tool body.

35. The milling tool of claim 1 wherein aligned formations are carried by the cover and the tool body, at least one movable member is movably carried by a selected one of the cover and the body, and the movable member releasably engages the aligned formations to establish a driving connection between the cover and the body.

36. The milling tool of claim 35 wherein the support means is rotatable about an axis, and the movable member is movable axially of the axis into and out of engagement with the aligned formations.

37. The milling tool of claim 36 wherein the movable member forms part of the cover.

38. The milling tool of claim 35 wherein the support means is rotatable about an axis, and the movable member is movable radially of the axis into and out of engagement with the aligned formations.

39. The milling tool of claim 35 wherein the support means is rotatable about an axis and the movable member is rotatable about the axis into and out of engagement with the aligned formations.

40. The milling tool of claim 35 wherein the support means is rotatable about a first axis, and the movable member is rotatable about a second axis to releasably establish a driving connection between the cover and the body.

41. The milling tool of claim 40 wherein the aligned formations carried by a selected one of the cover and the body comprise slots, and the aligned formations carried by the other of the cover and the body are flats formed on a rotatable rod.

42. The milling tool of claim 35 additionally including biasing means biasing the movable member toward a position where the movable member engages the aligned formations.

43. The milling tool of claim 35 wherein a threaded connection is additionally formed between the support means and the tool body.

44. The milling tool of claim 35 additionally including detent means associated with the movable member to assist in retaining the movable member in a position of engagement with the aligned formations.

45. The milling tool of claim 1 wherein mating formations are carried on the body and on the support means for releasably drivingly connecting the body and the support means, and such of said formations as are carried on a selected one of the body and the support means are resiliently deformable to facilitate retaining a secure mating engagement between the mating formations.

46. The milling tool of claim 1 wherein the tool support means includes a rotatable hub and a rotatable drive shaft, the cover and the tool body are supported on the hub, and a releasable driving connection is formed between the hub and the drive shaft.

47. The milling tool of claim 1 wherein a rod is rotatably carried by a selected one of the support means and the body, flats are formed on the rod, at least one slot-like formation is carried on the other of the support means and the body, and the flattened portions of the rod are insertable into the slot-like formation whereafter the rod can be rotated to releasably retain the rod in the slot-like formation, whereby the engagement of the rod and the slots establishes a connection between the support means and the body.

48. A milling tool for use in milling tissues from a joint socket in the prosthetic replacement of a joint, comprising:
   a. a body having first wall portions which define a substantially hemispherical outer surface, second wall portions which define a cavity located inside the outer surface, and third wall portions which define an opening through the body communicating with the cavity;
   b. a plurality of blades carried on the first wall portions in spaced relationship around the outer surface;
   c. a plurality of holes formed through the body, each of the holes having one end which opens through the first wall portions near a separate one of the blades, and having another end which opens through the second wall portions in communication with the cavity; and,
   d. tool support means drivingly connected to the body and including a cover which releasably closes the opening defined by the third wall portions.

49. The milling tool of claim 48 wherein mating formations are carried on the body and on the support means for releasably drivingly connecting the body and the support means.

50. The milling tool of claim 48 additionally including a locking member movably carried by a selected one of the support means and the body for releasably retaining mating engagement between the mating formations.

51. The milling tool of claim 50 additionally including biasing means carried by a selected one of the support means and the body for releasably retaining the movable locking member in a locked position.

52. The milling tool of claim 48 wherein a driving connection is established between the tool support means and the tool body by means of at least one latch formation carried on a selected one of the support means and the body, and by at least one latch member which is movably carried by the other of the support means and the body and which is releasably engagable with the latch formation.

53. The milling tool of claim 48 wherein aligned formations are carried by the cover and the tool body, at least one movable member is movably carried by a selected one of the cover and the body, and the movable member releasably engages the aligned formations to establish a driving connection between the cover and the body.

54. The milling tool of claim 48 wherein the tool support means includes a rotatable hub and a rotatable drive shaft, the cover and the tool body are supported on the hub, and a releasable driving connection is formed between the hub and the drive shaft.

* * * * *